(12) United States Patent
Kim

(10) Patent No.: US 9,314,570 B2
(45) Date of Patent: *Apr. 19, 2016

(54) FILTER NEEDLE

(71) Applicant: ZAMART CO., LTD, Seoul (KR)

(72) Inventor: Keun-Bae Kim, Seoul (KR)

(73) Assignee: ZAMART CO., LTD, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/498,614

(22) Filed: Sep. 26, 2014

(65) Prior Publication Data

US 2015/0045738 A1 Feb. 12, 2015

Related U.S. Application Data

(63) Continuation of application No. 14/009,240, filed as application No. PCT/KR2012/002632 on Apr. 6, 2012.

(30) Foreign Application Priority Data

| Apr. 8, 2011 | (KR) | 10-2011-0032459 |
| Apr. 8, 2011 | (KR) | 10-2011-0032465 |
| Jul. 11, 2011 | (KR) | 10-2011-0068521 |
| Oct. 31, 2011 | (KR) | 10-2011-0112458 |

(51) Int. Cl.
*A61M 5/165* (2006.01)
*A61M 5/31* (2006.01)
*A61M 5/32* (2006.01)
*A61M 5/34* (2006.01)

(52) U.S. Cl.
CPC ............ *A61M 5/165* (2013.01); *A61M 5/3145* (2013.01); *A61M 5/329* (2013.01); *A61M 5/34* (2013.01)

(58) Field of Classification Search
CPC ..... A61M 5/3145; A61M 5/329; A61M 5/34; A61M 5/165
USPC ........... 604/36, 122, 181, 187, 190, 247, 240; 137/846, 493.8, 493.9, 550
See application file for complete search history.

(56) References Cited

U.S. PATENT DOCUMENTS 4,332,249 A * 6/1982 Joslin ................. A61M 5/3145
604/36
6,796,965 B2 * 9/2004 Dumaresq-Lucas et al. . 604/190

FOREIGN PATENT DOCUMENTS

JP 2003-339876 A 12/2003
KR 10-0628364 B1 9/2006

* cited by examiner

*Primary Examiner* — Theodore Stigell
*Assistant Examiner* — Amber Stiles
(74) *Attorney, Agent, or Firm* — Jefferson IP Law, LLP

(57) ABSTRACT

A filter needle for a syringe including a syringe needle having a needle, a fixing member for fixing the needle and an inner space formed in the fixing member, and a syringe body having a cylinder, a piston and a front end separably installed in the inner space of the fixing member of the syringe needle, is provided. The filter needle includes a filter structure installed in the inner space of the fixing member of the syringe needle and including an one-way inlet path having an inlet and an one-way outlet path having an outlet, each of which has a check valve function, and a filter installed in the outlet path at a rear end of the outlet to filter a foreign substance, which is input through the inlet together with a medicament liquid, from the medicament liquid such that the medicament liquid is only injected into a patient through the outlet when injecting the medicament liquid into the patient.

11 Claims, 30 Drawing Sheets

FILTER NEEDLE

CROSS-REFERENCE TO RELATED APPLICATION(S)

This is a continuation application of prior U.S. patent application Ser. No. 14/009,240, filed on Oct. 1, 2013, which claims the benefit under 35 U.S.C. §371 of an International application filed on Apr. 6, 2012 and assigned application number PCT/KR2012/002632, which claimed the benefit of a Korean patent application filed on Apr. 8, 2011, in the Korean Intellectual Property Office and assigned Serial number 10-2011-0032459, a Korean patent application filed on Apr. 8, 2011, in the Korean Intellectual Property Office and assigned Serial number 10-2011-0032465, a Korean patent application filed on Oct. 31, 2011, in the Korean Intellectual Property Office and assigned Serial number 10-2011-0112458, and a Korean patent application filed on Jul. 11, 2011, in the Korean Intellectual Property Office and assigned Serial number 10-2011-0068521, the entire disclosures of which are incorporated herein by reference in their entirety.

TECHNICAL FIELD

The present invention relates to a medical filter needle, and more particularly, to a filter needle which is detachably installed to a syringe consisting of a cylinder and a piston in use in order to prevent a fine powder, which is generated from a glass or plastic ampoule, from being injected into a patient when the medicament liquid of the ampoule made of glass or plastic, which is absorbed into the cylinder of the syringe, is injected through a syringe needle.

In addition, the present invention is provided for allowing the chemical liquid of the ampoule made of glass or plastic to be easily absorbed into the cylinder of a syringe and to be easily injected into a patient.

BACKGROUND ART

In general, a syringe, which includes a syringe body and a syringe needle separably installed to a front end of the syringe body, is used for directly injecting a medicament liquid into a patient in a hospital. Since most patients are contaminated with various viruses replicating in living cells as the smallest microorganisms or germs (bacteria) and specifically pathogenic bacteria harmful to a human body, which are fine single-celled organisms, a disposable syringe is mandatorily used to prevent secondary infection during injection.

However, except for solid injection requiring injection distilled water for dissolving the solid injection or diluting water-soluble injection, most of injections used in the disposable syringe are made in a liquid state and contained in glass or plastic ampoules. The injections required to be kept for a long time are made in the form of a solid so as to be dissolved in use and are contained and preserved in ampoules, so the injections are used after being mixed with injection distilled water.

Impurity powder, such as glass powder (the particle size of ~70 μm) or plastic powder (which is finer than the glass powder), is generated when the ampoule is opened for injection. In this state, when the medicament liquid contained in the ampoule or the mixture of the injection distilled water and the solid injection is sucked into the syringe body by using the needle (which is standardized and, in general, has an outer diameter of 652 μm) of the syringe needle, various powder or impurities generated when opening the ampoule are sucked simultaneously with the medicament liquid and the mixture, so that the powder or impurities may be injected into a human body together with the medicament liquid.

Thus, the injected impurities, in particular, glass particles of the injected impurities move along a blood vessel, thereby causing necrosis, lung granuloma, phlebitis and thrombosis. In extreme case, a cancer may be caused. That is, the injected impurities may cause many side effects.

Therefore, as shown in FIGS. 8 and 9, there has been recently proposed a filter needle including a filter 300 installed in the fixing member 220 for fixing a needle 210 in order to separably install a syringe needle 200 to a front of a syringe, so that the filter 300 may filter impurities such as a glass or plastic powder or an impurity powder generated in opening an ampoule.

In this case, if the syringe needle is not exchanged on time, the impurities attached to the filter may be injected into a patient through the syringe needle.

Practically, in the medical field, the syringe needle 200, to which the filter 300 is installed, is used to suck the medicament liquid through the syringe needle into the syringe body 100 having the cylinder 110 and the piston 120, and then, the syringe needle 200 is replaced with new one to inject the medicament liquid into a patient.

However, in this case, the medicament liquid is exposed to air so that the medicament liquid may be oxidized or infected. In addition, this sequence of woks is very complicated to medical workers and makes it difficult to rapidly treat emergency patients. Further, many disposable syringes are used even for one day and plural syringe needles are used at one time of injection, so that medical wastes are exponentially increased, thereby exerting harmful influence on environment.

Specifically, these medical syringe wastes must be treated after being separated from general medical wastes, so that the cost for treating the medical waste is increased.

DISCLOSURE TECHNICAL PROBLEM

Therefore, the present invention provides a filter needle which can filter impurities without exchanging a syringe needle, can be easily assembled to be provided at a low cost, and can disperse an injection pressure to easily perform injection.

In accordance with an embodiment of the present disclosure, a filter needle for a syringe is provided. The filter needle for a syringe includes a syringe needle having a needle, a fixing member for fixing the needle and an inner space formed in the fixing member, and a syringe body having a cylinder, a piston and a front end separably installed in the inner space of the fixing member of the syringe needle. The filter needle includes a filter structure installed in the inner space of the fixing member of the syringe needle and including an one-way inlet path having an inlet and an one-way outlet path having an outlet, each of which has a check valve function, and a filter installed in the outlet path at a rear end of the outlet to filter a foreign substance, which is input through the inlet together with a medicament liquid, from the medicament liquid such that the medicament liquid is only injected into a patient through the outlet when injecting the medicament liquid into the patient.

To this end, the present invention provides a filter structure, which has one-way paths having an inlet and an outlet having a check valve function and installed in a fixing member which is separably installed to a front of a syringe body to fix a needle of a syringe needle, and a filter installed to a front end of the outlet of the filter structure, such that, when a medicament liquid sucked together with impurities is injected into a patient, the medicament liquid is only injected through the outlet while the impurities are being filtered by the filter.

Further, the inlet and outlet having the check valve function have a structure capable of complementing the check valve function and allowing the suction and exhaustion to be easily performed while preventing the check valve function from being deteriorated in the suction and exhaustion.

In addition, a cross-sectional area of the filter is changed to reduce the pressure when the medicament liquid input through the inlet is injected, so that the pressure is dispersed during the exhaustion (injection).

In addition, the filter structure is injection-molded into a single body, so that easy fabrication, precise filtering and product uniformity can be achieved.

Further, the filter structure is simplified and the structure of the fixing member separably installed to the front of the syringe body is changed while the needle of the syringe needle is fixed, so that the filter structure is easily fabricated and the pressure is minimized when the medicament liquid is exhausted through the outlet for injection.

As described above, according to the present invention, the paths of sucking and exhausting a medicament liquid are separated from each other, so that there is no need to exchange a syringe needle and impurities are filtered by the filter only when exhausting the medicament liquid and there is no concern about the injection of impurities into a patient. In addition, the cross-sectional area of the filter is enlarged, so that the injection can be easily operated.

In addition, according to the present invention, the filter structure, to which the filter is installed, is only installed to the fixing member of the syringe needle so that the filter needle can be applied to the existing syringes. Thus, the filter needle can be easily fabricated and assembled at a low cost.

Figure 1:
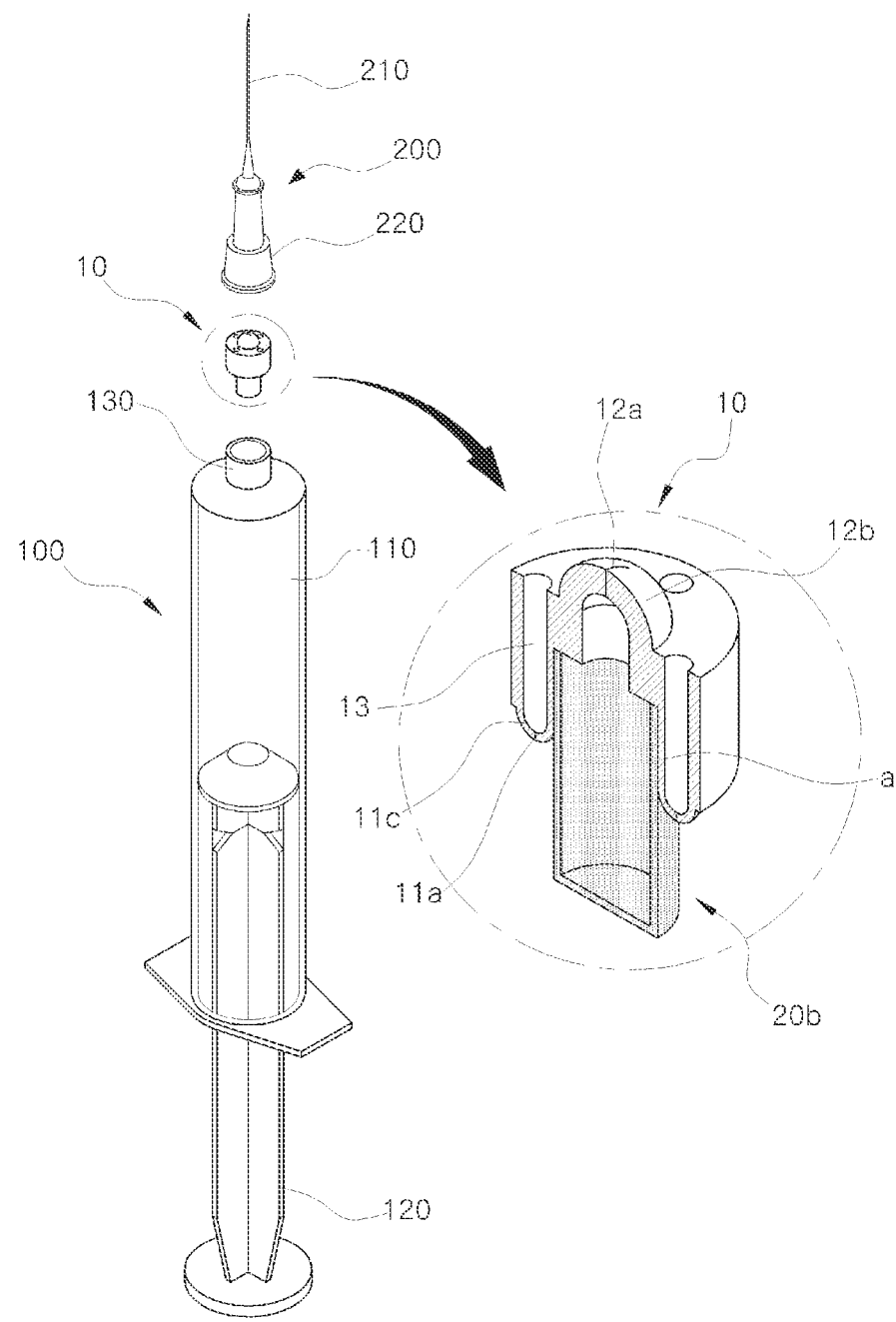
FIG. 1 is a perspective view showing a closed filter structure according to an embodiment of the present invention.

A filter needle for a syringe is provided. The syringe includes a syringe needle 200 having a needle 210, a fixing member 220 for fixing the needle 210 and an inner space 230 formed in the fixing member 220, and a syringe body 100 having a cylinder 110, a piston 120 and a front end 130 separably installed in the inner space 230 of the fixing member 220 of the syringe needle 200. The filter needle includes a filter structure 10 installed in the inner space (230) of the fixing member (220) of the syringe needle 200 and including an one-way inlet path (13) having an inlet (11) and an one-way outlet path (14) having an outlet (12), each of which has a function of a check valve; and a filter (20) installed in the outlet path (14) at a rear end of the outlet (12) to filter a foreign substance, which is input through the inlet (11) simultaneously together with a medicament liquid, from the medicament liquid such that the medicament liquid is only injected into a patient through the outlet (12) when injecting the medicament liquid into the patient.

Hereinafter, an exemplary embodiment of the present invention will be described in detail with reference to accompanying drawings. The same reference numerals will be used to refer to the same elements throughout the drawings. In a description of the embodiment, if the function or the structure related to the disclosure and generally known to those skilled in the art make the subject matter of the disclosure unclear, the details of the function or the structure will be omitted. It should be understood that, although the exemplary embodiment of the present invention is described hereinafter, the technical spirit of the present invention is not limited thereto, and can have various modifications. FIGS. 1, 5, 9, 13, 18, 22 and 28 are exploded views showing various types of syringes, each of which has a liquid path. FIGS. 2, 6, 10, 14, 19, 23 and 29 are sectional views showing states that a filter needle is installed to a syringe. FIGS. 3, 7, 11, 15, 20, 24 and 30 are views showing states that a medicament liquid is sucked through a filter needle. FIGS. 4, 8, 12, 16, 21, 25 and 31 are views showing states that a medicament liquid is exhausted through a filter needle.

Currently, a general-used syringe includes a syringe body 100 and a syringe needle 200. The syringe body 100 has a front end 130 protruding in a front direction such that the syringe needle 200 is separably installed a cylinder 110, in which a piston 120 reciprocates, in the front direction of the cylinder 110. That is, the syringe needle 200 is separably installed to the front end 130 of the syringe body 100. The syringe needle 200 includes a needle 210 and a fixing member 220. The needle 210 is generally formed of a metallic material. The fixing member 220 is integrated with the needle 210 to fix the needle thereto (which is generally formed through an insert injection molding scheme for tight fixing) and has an inner space 230 in which the needle 210 is separably installed to the front end 130 of the syringe body 100.

A filter structure 10 of the present invention applied to the syringe is installed at an inside, that is, in an inner space of the fixing member 220 which fixes the needle 210 of the syringe needle 200 thereto. The front end 130 of the syringe body 100 is installed to a rear end of the filter structure 10 such that the filter structure 10 is prevented from being voluntarily separated from the inner space 230 of the fixing member 220 even when a medicament liquid is sucked through the needle 210.

Further, in the filter needle of the present invention, the filter structure 10, which is installed in the inner space 230 of the fixing member 220 of the syringe needle 200, is coupled to be prevented from being voluntarily separated from the inner space 230.

Further, the filter structure 10 of the present invention may include closed inlet and outlet paths 13 and 14 which are separated from each other, and may be tightly closed and installed to an inner wall 230a of the fixing member 220 of the syringe needle 200. Differently, the filter structure 10 may include an opened inlet path 13a and the closed outlet path 14 and is tightly closed to the fixing member 220 by a guide groove 230b which is formed on the inner wall 230a which forms the inner space 230 of the fixing member 220, so that a closed inlet path may be formed, so the filter structure 10 may be simplified.

The filter structure 10 is integrally formed by molding medical silicon which is harmless to a human body and has excellent heat resistance, elasticity and abrasion resistance.

Of course, it is possible in the scope of the objects of the present invention to substitute various materials for the medical silicon.

In addition, the filter structure 10 installed to the syringe needle 200 has the inlet 11 and the outlet 12 having a check valve function and further, has one-way paths, that are, the inlet and outlet paths 13 and 14 having a predetermined depth in the rear direction of the filter structure 10. A filter 20 is only installed at a rear end of the outlet 12, that is, in the outlet path 14, so that the medicament liquid from which a foreign substance, which is input through the inlet 11 simultaneously together with the medicament liquid, is filtered, is only injected through the outlet 12.

The closed outlet path 14 is provided at the center of the simplified filter structure 10 and the opened inlet path 13a having no check valve function is formed at the periphery of the closed outlet path 14. An inclined film 11a-1 folded by a pressure is formed on the rear end of the opened inlet path 13a. The simplified filter structure 10 is tightly coupled to the inner wall 230a which forms the inner space 230 of the fixing member 220 of the syringe needle 200, so that one-way closed inlet path is formed in the inner wall 230 by the guide groove 230b having a predetermined width and depth and the inlet 11a having the check valve function is formed at the rear end thereof.

Although it is possible to form the filter structure 10 in an assembly type, if taking into consideration economic efficiency or product completion, it is preferable to fabricate the filter structure 10 in an integral type. Thus, the integral type of the filter structure 10 will be described in the embodiment.

Further, although the inlet path of the filter structure 10 according to the present invention may be in an open or close type 13 or 13a, the outlet path 14 must be only in a close type.

Hereinafter, a preferable embodiment according to the present invention will be described with reference to accompanying drawings in detail.

Figure 5:
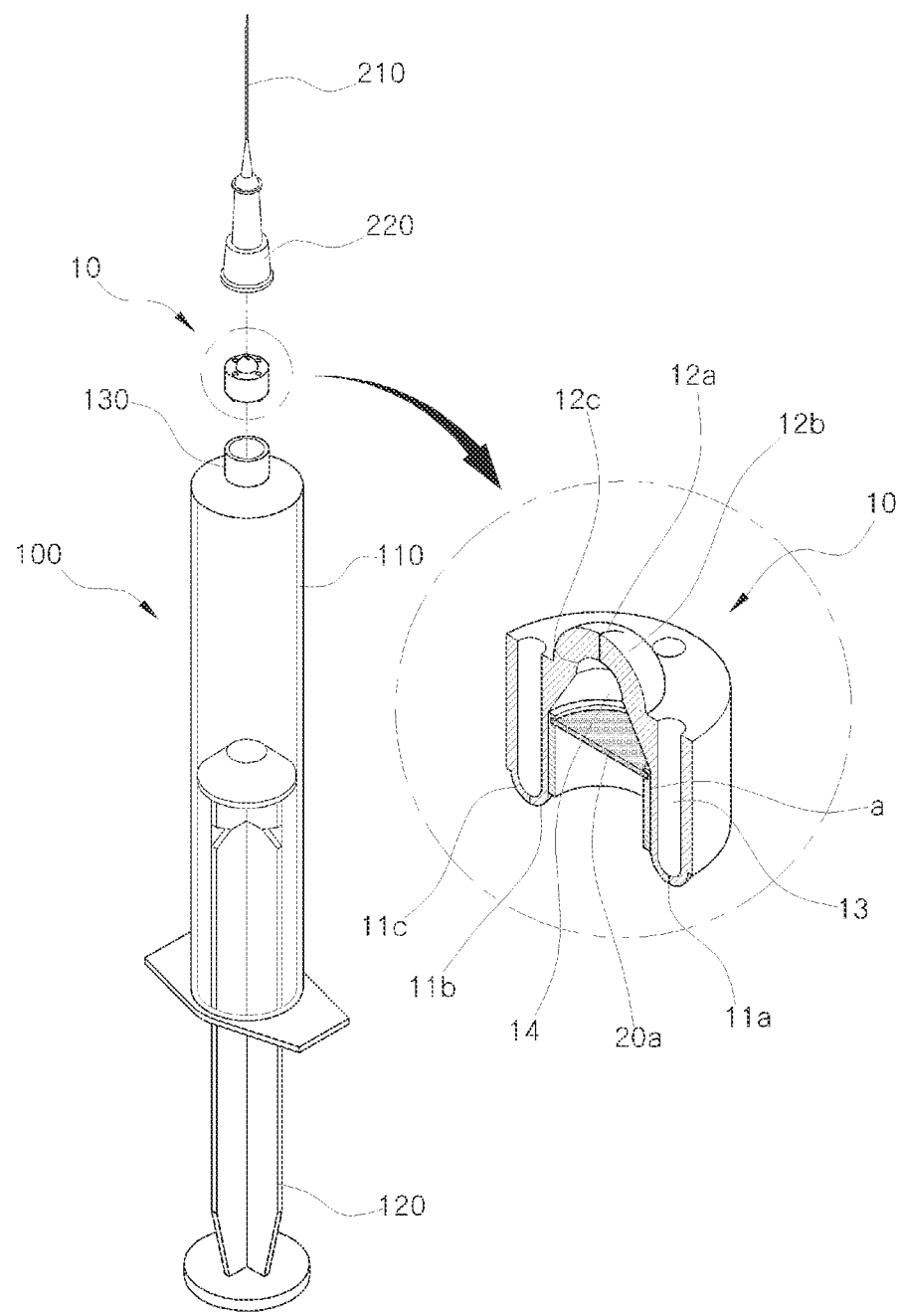
FIG. 5 is a perspective view showing a closed filter structure according to another embodiment of the present invention.
Figure 6:
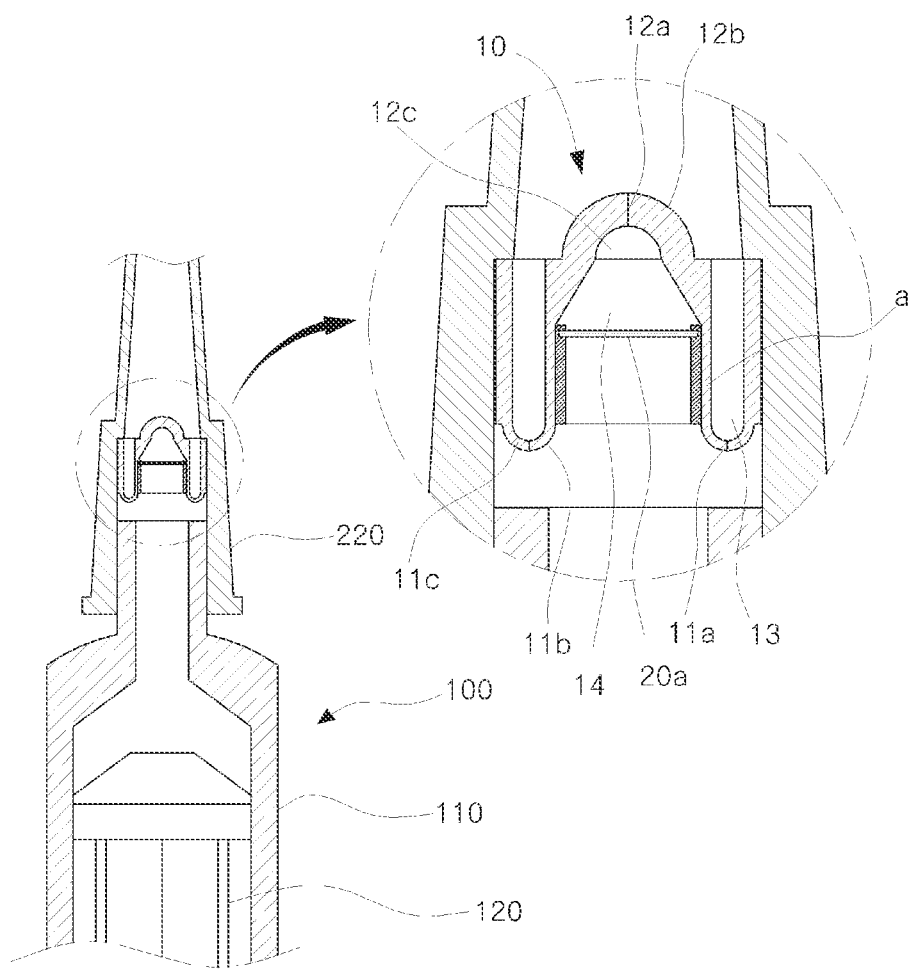
FIG. 6 is a sectional view showing a state that the filter structure of FIG. 5 is installed to a syringe.
Figure 7:
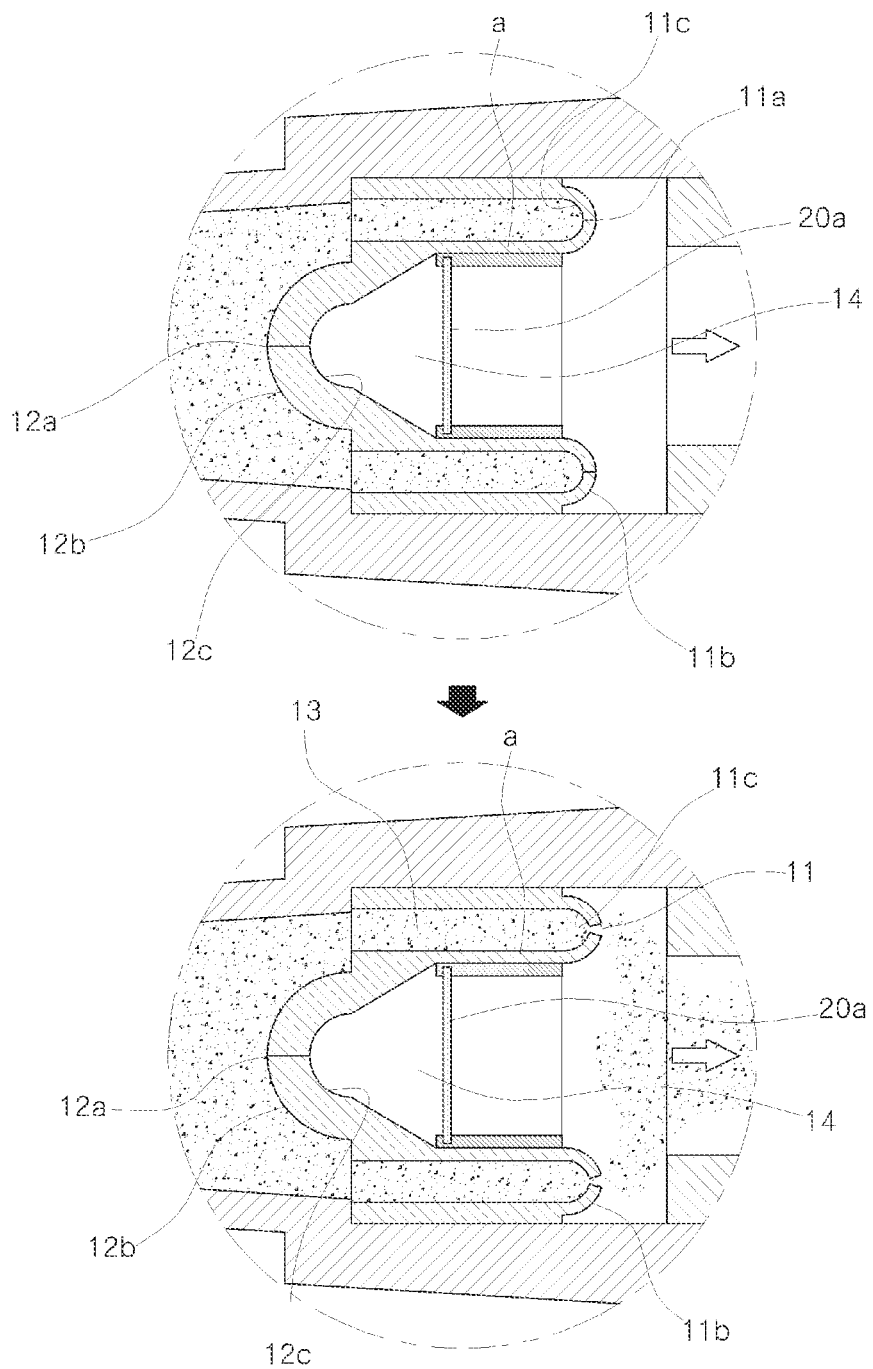
FIG. 7 is a view showing a state that a medicament liquid flows into an inlet path of the filter structure of FIG. 5.
Figure 8:
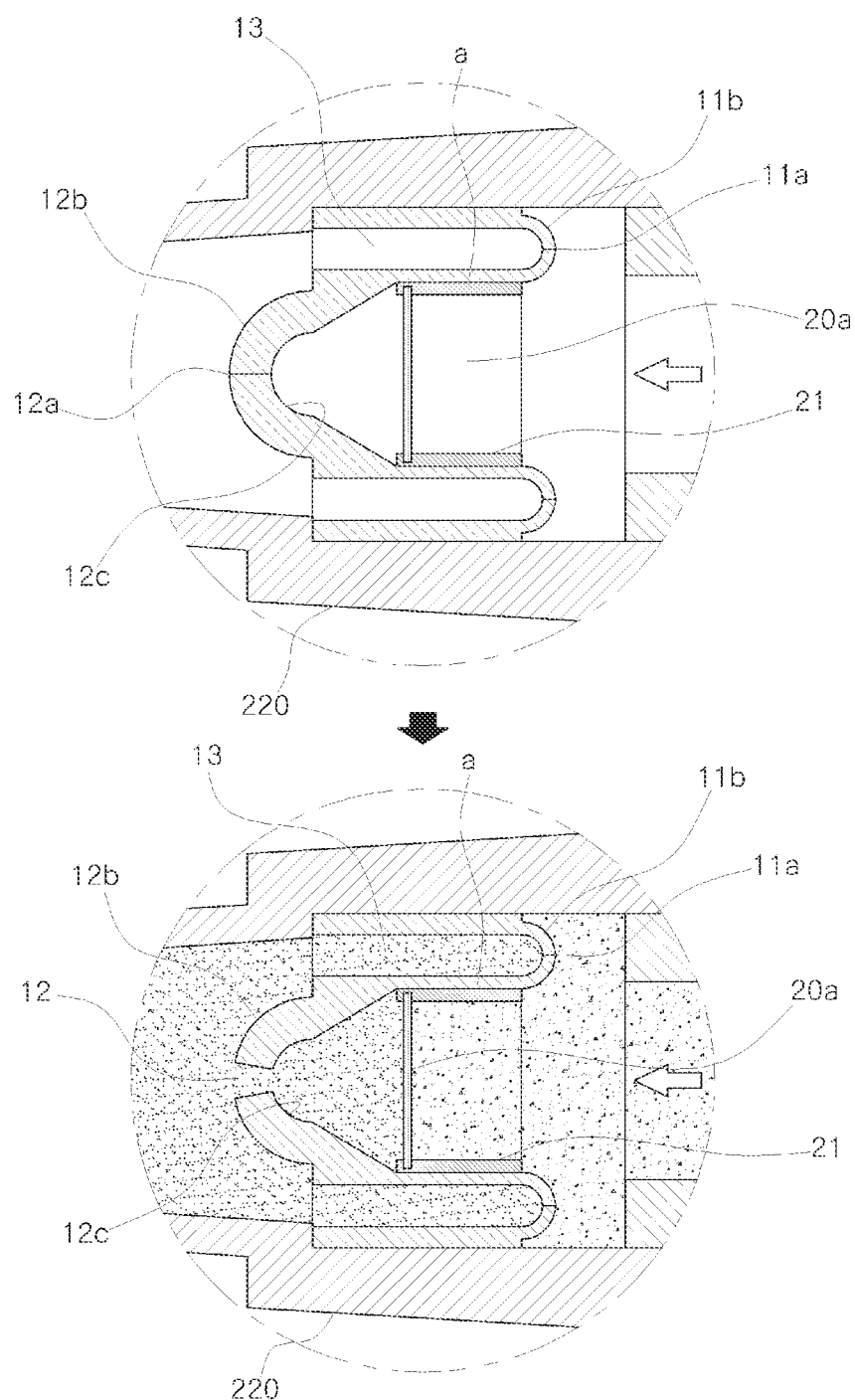
FIG. 8 is a view showing a state that a medicament liquid is exhausted through an outlet path of the filter structure of FIG. 5.
Figure 9:
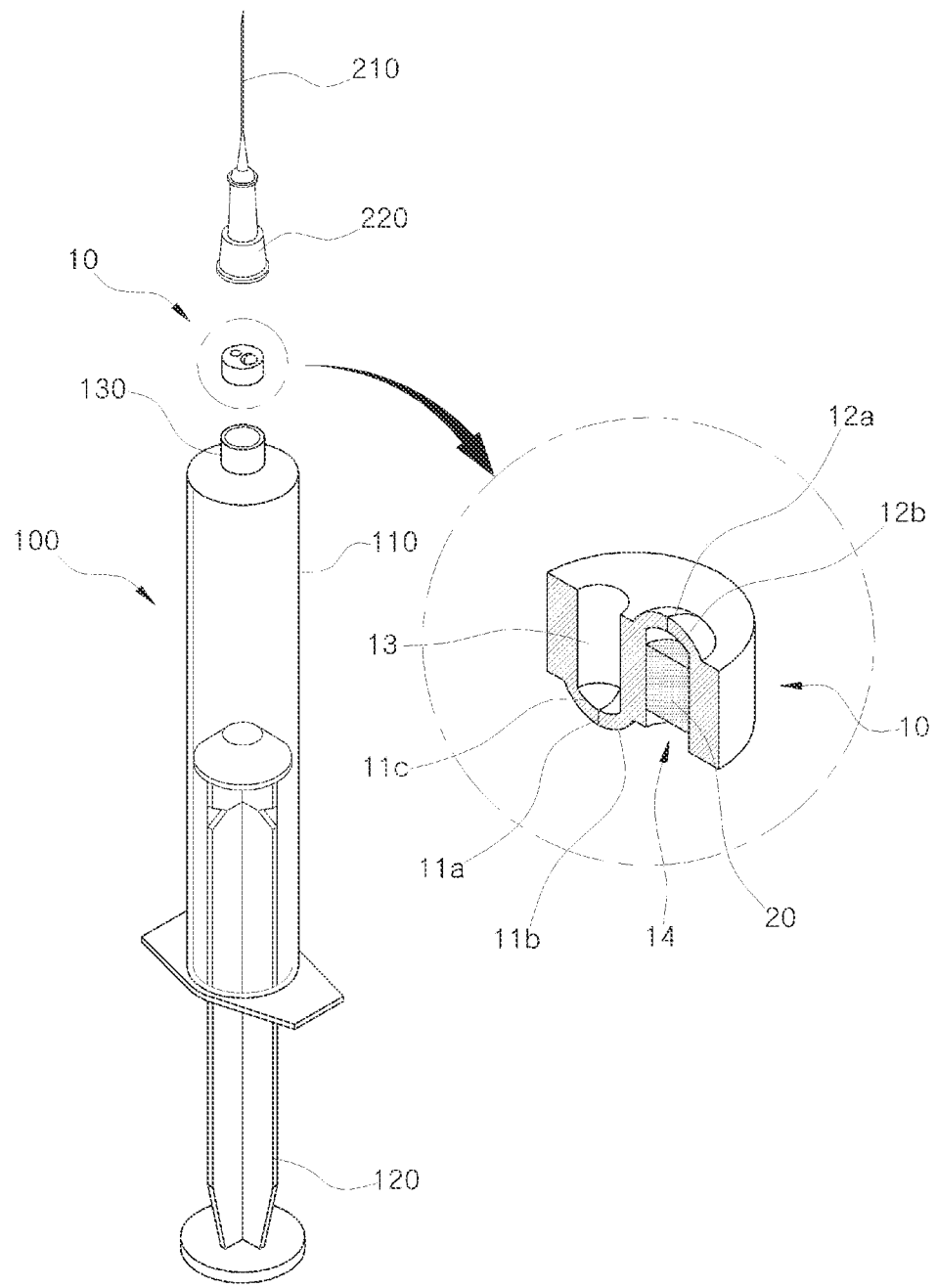
FIG. 9 is a perspective view showing a closed filter structure according to a third embodiment of the present invention.
Figure 10:
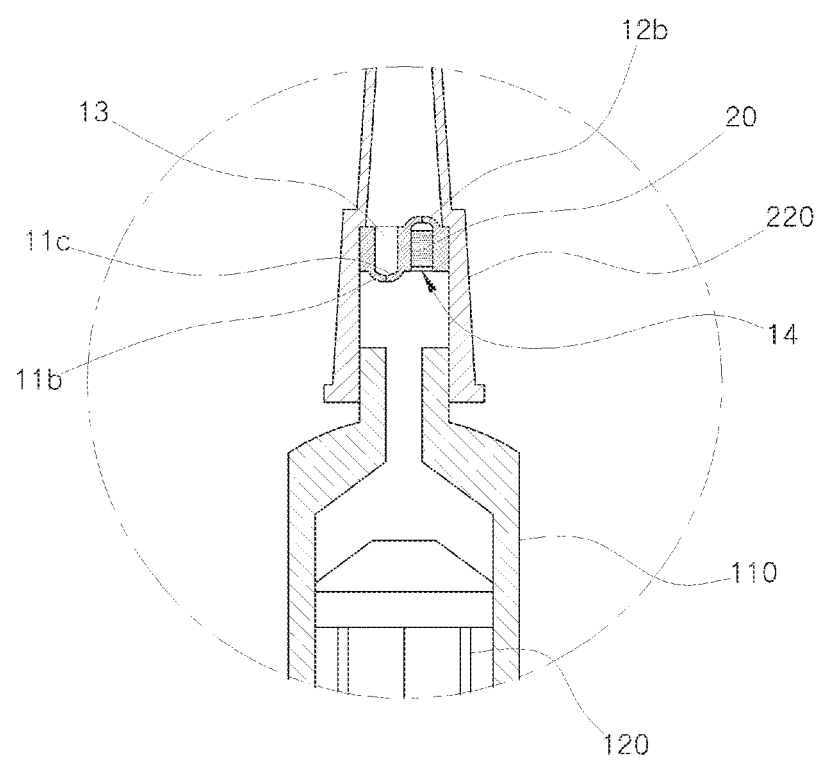
FIG. 10 is a sectional view showing a state that the filter structure of FIG. 9 is installed to a syringe.
Figure 11:
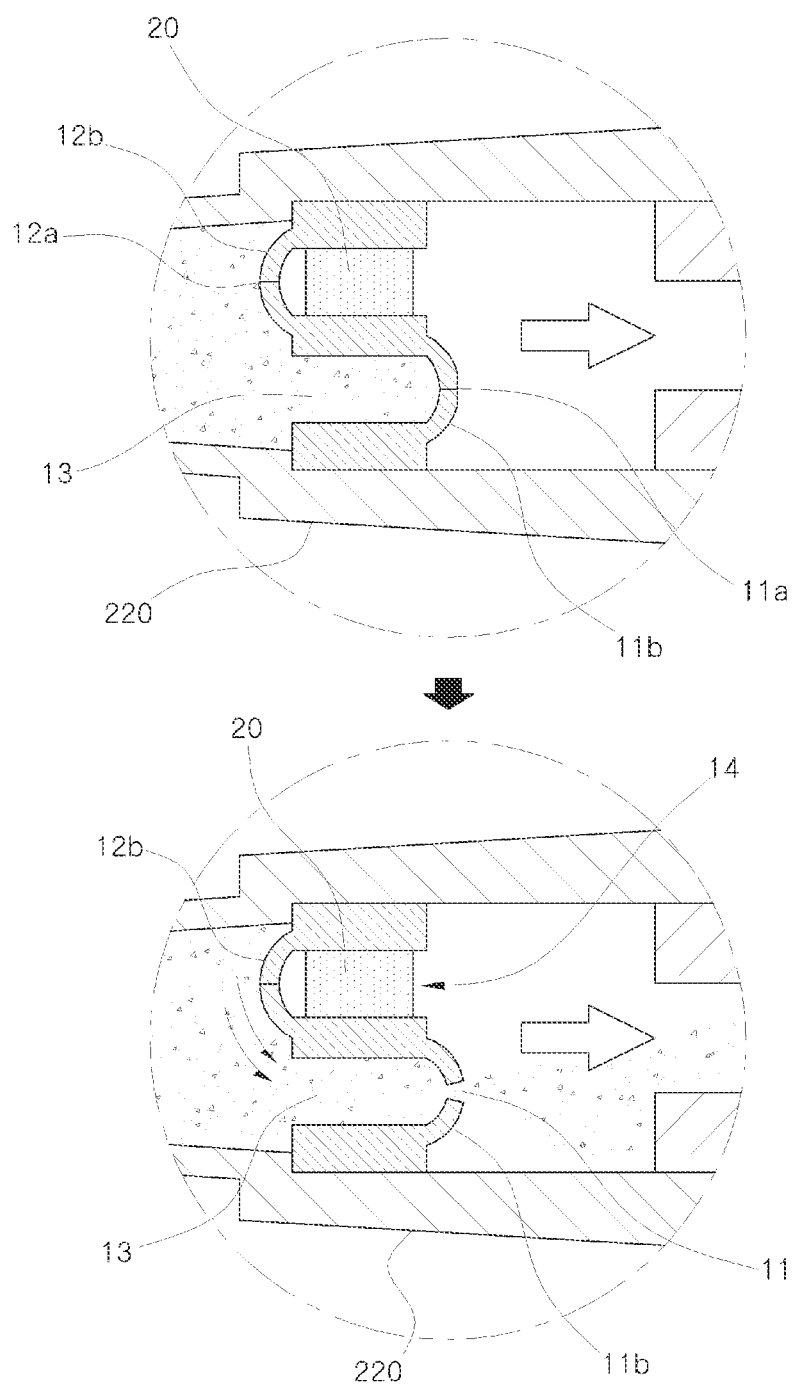
FIG. 11 is a view showing a state that a medicament liquid flows into an inlet path of the filter structure of FIG. 9.
Figure 12:
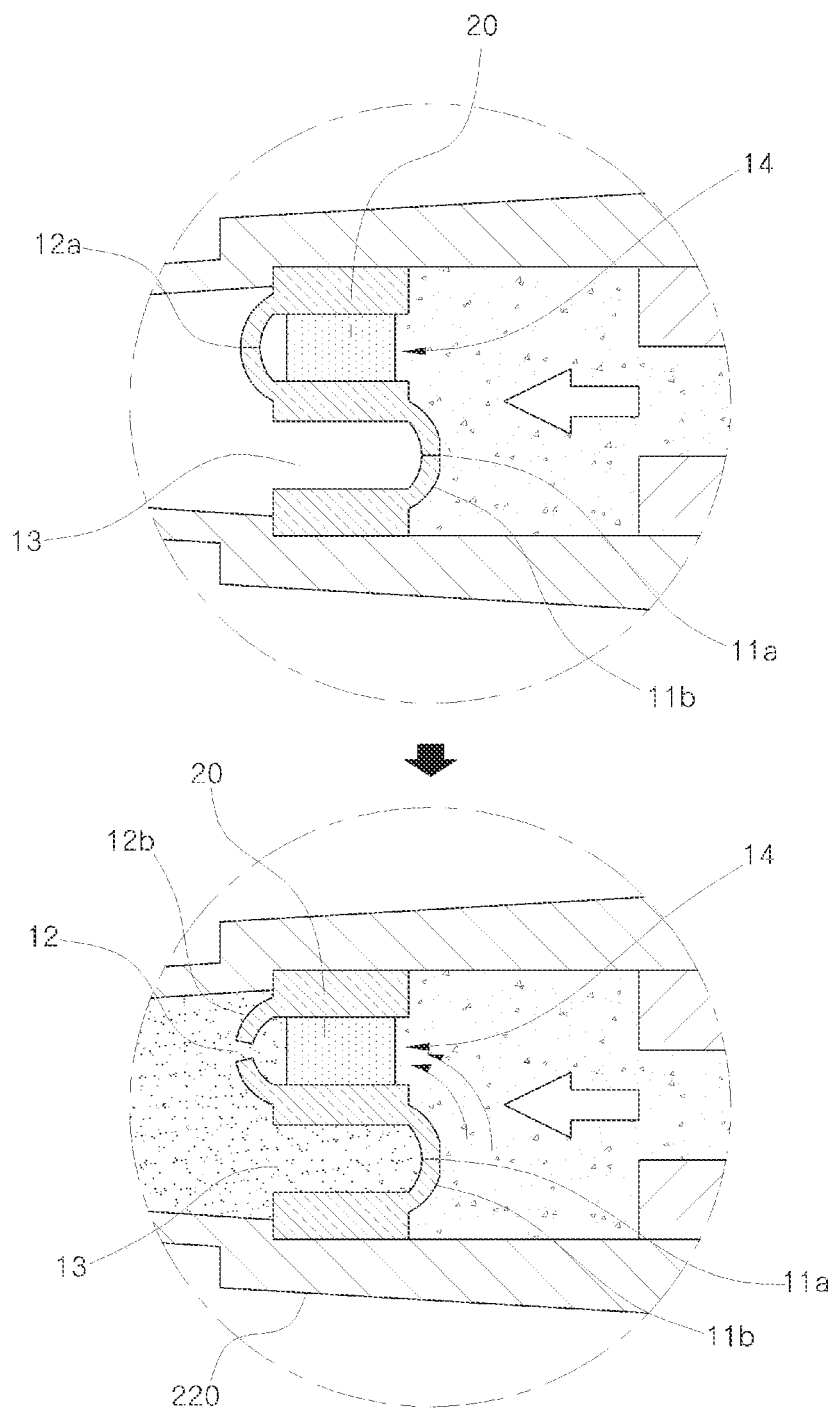
FIG. 12 is a view showing a state that a medicament liquid is exhausted through an outlet path of the filter structure of FIG. 9.
Figure 13:
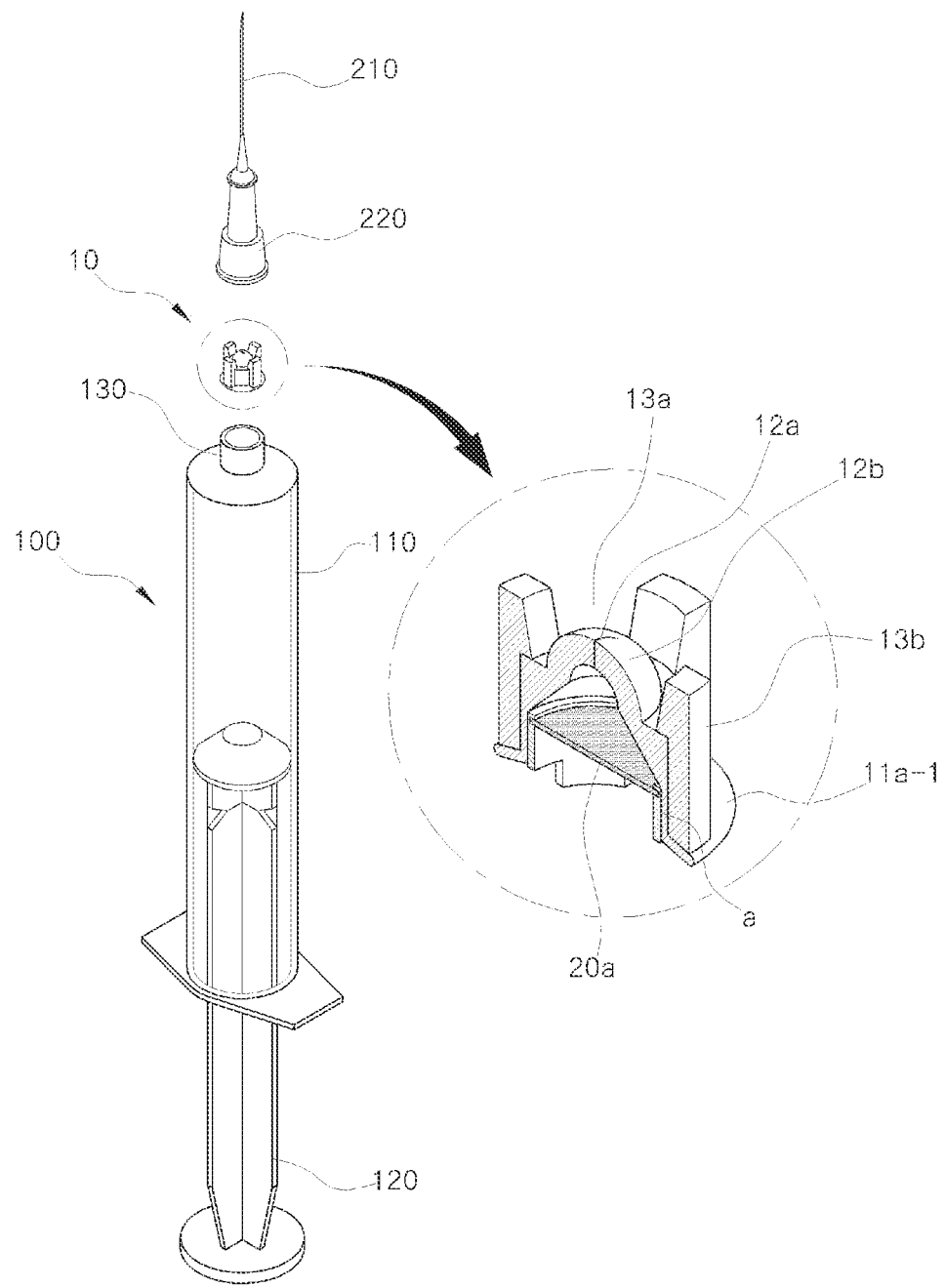
FIG. 13 is a perspective view showing an opened filter structure according to an embodiment of the present invention.
Figure 14:
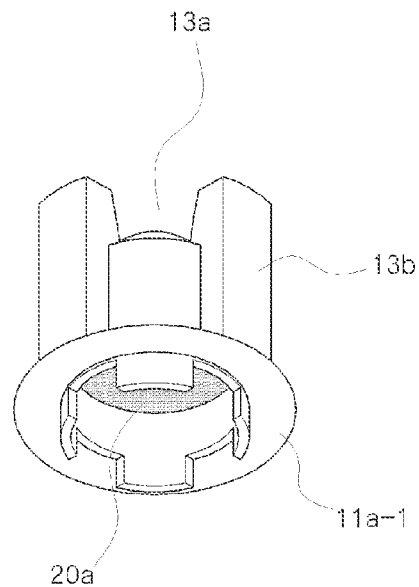
FIG. 14 is a sectional view showing a state that the filter structure of FIG. 13 is installed to a syringe.
Figure 15:
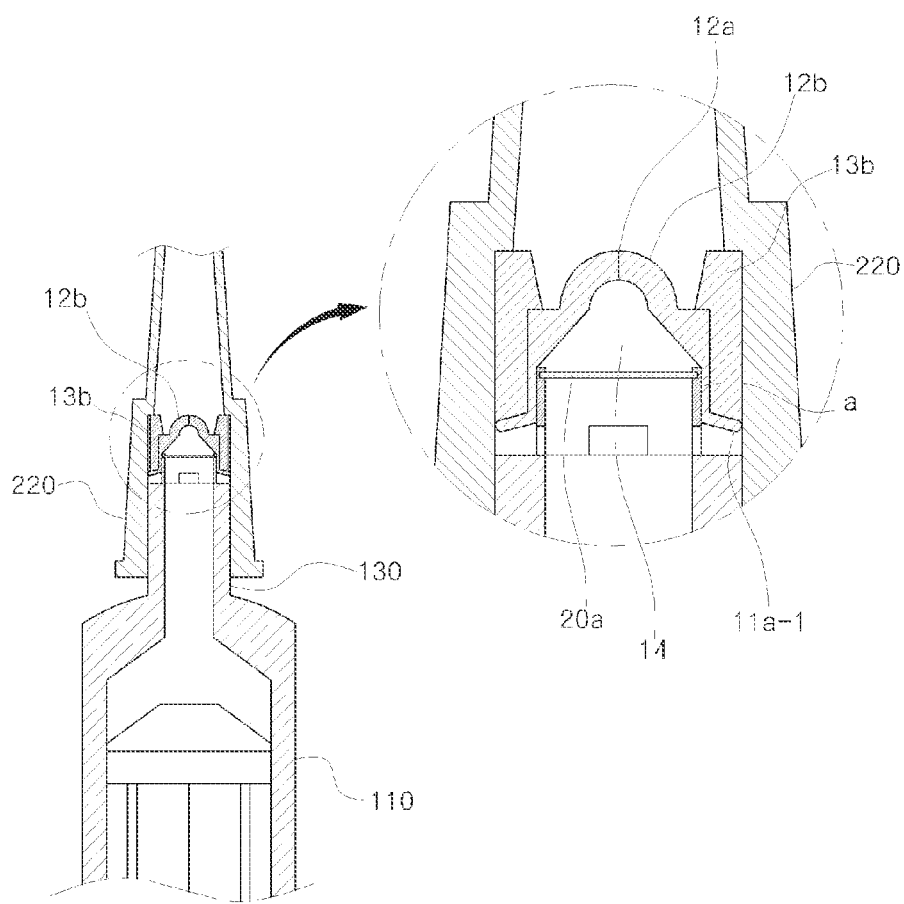
FIG. 15 is a view showing a state that a medicament liquid flows into an inlet path of the filter structure of FIG. 13.
Figure 16:
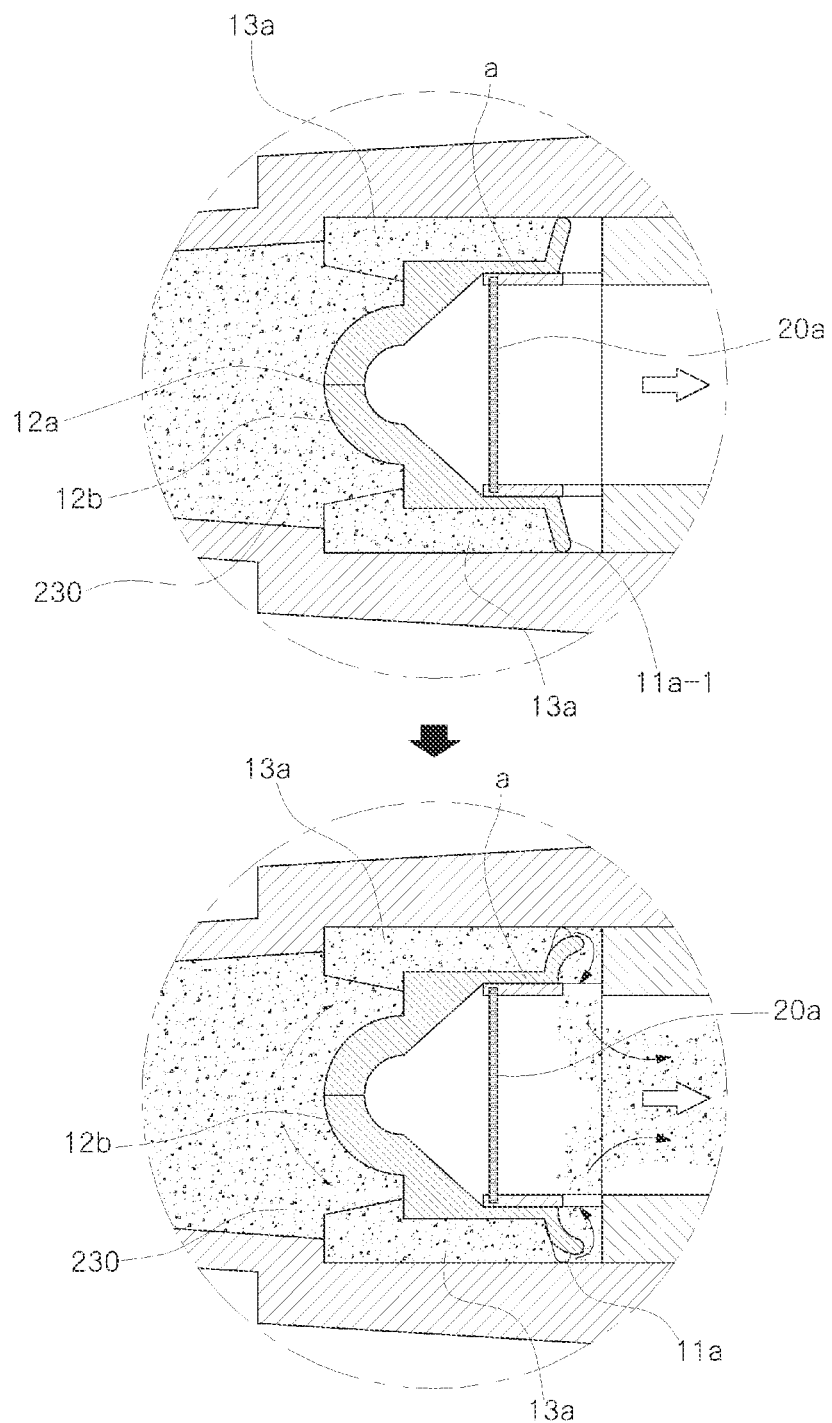
FIG. 16 is a view showing a state that a medicament liquid is exhausted through an outlet path of the filter structure of FIG. 13.
Figure 17:
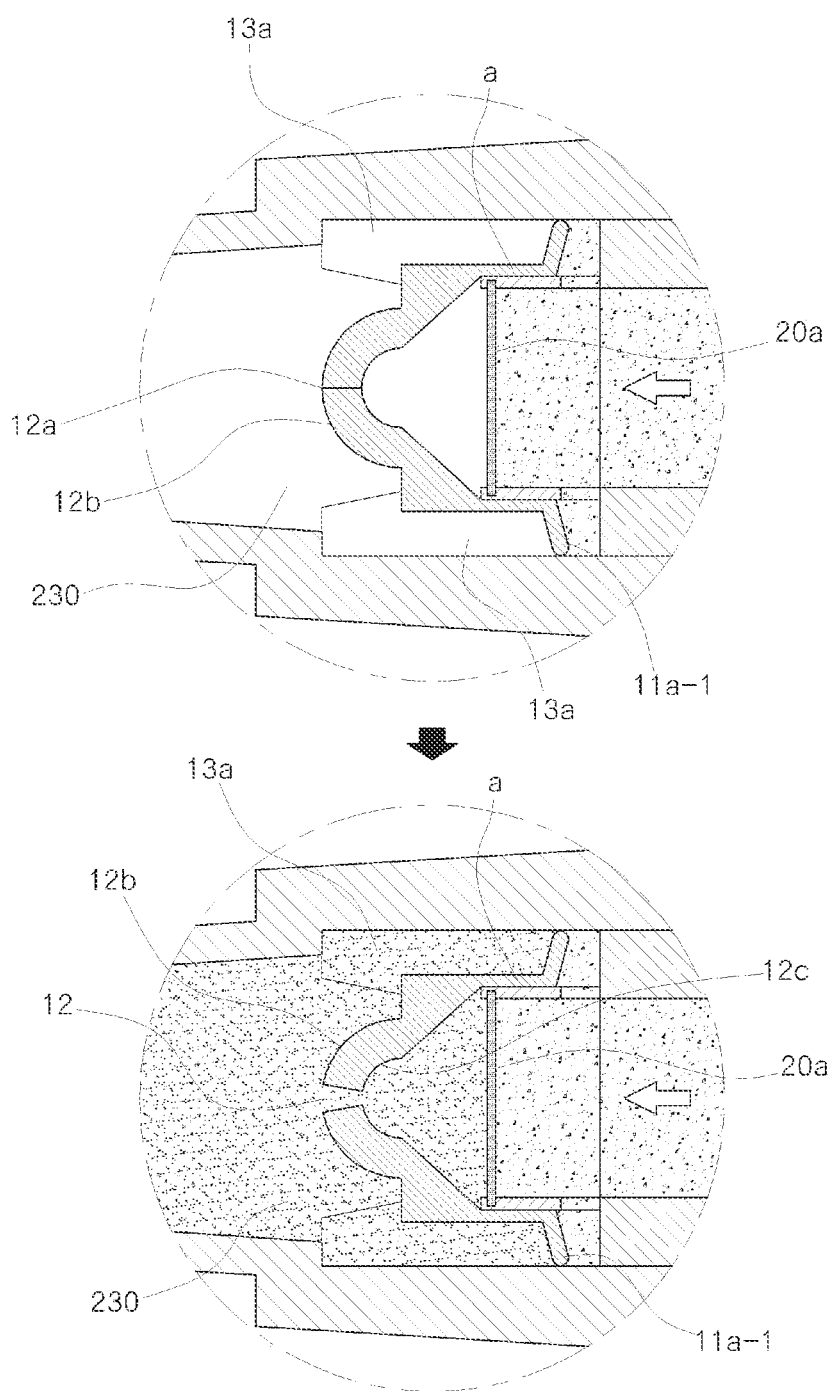
FIG. 17 is a perspective view showing an appearance of the filter structure of FIG. 13.
Figure 18:
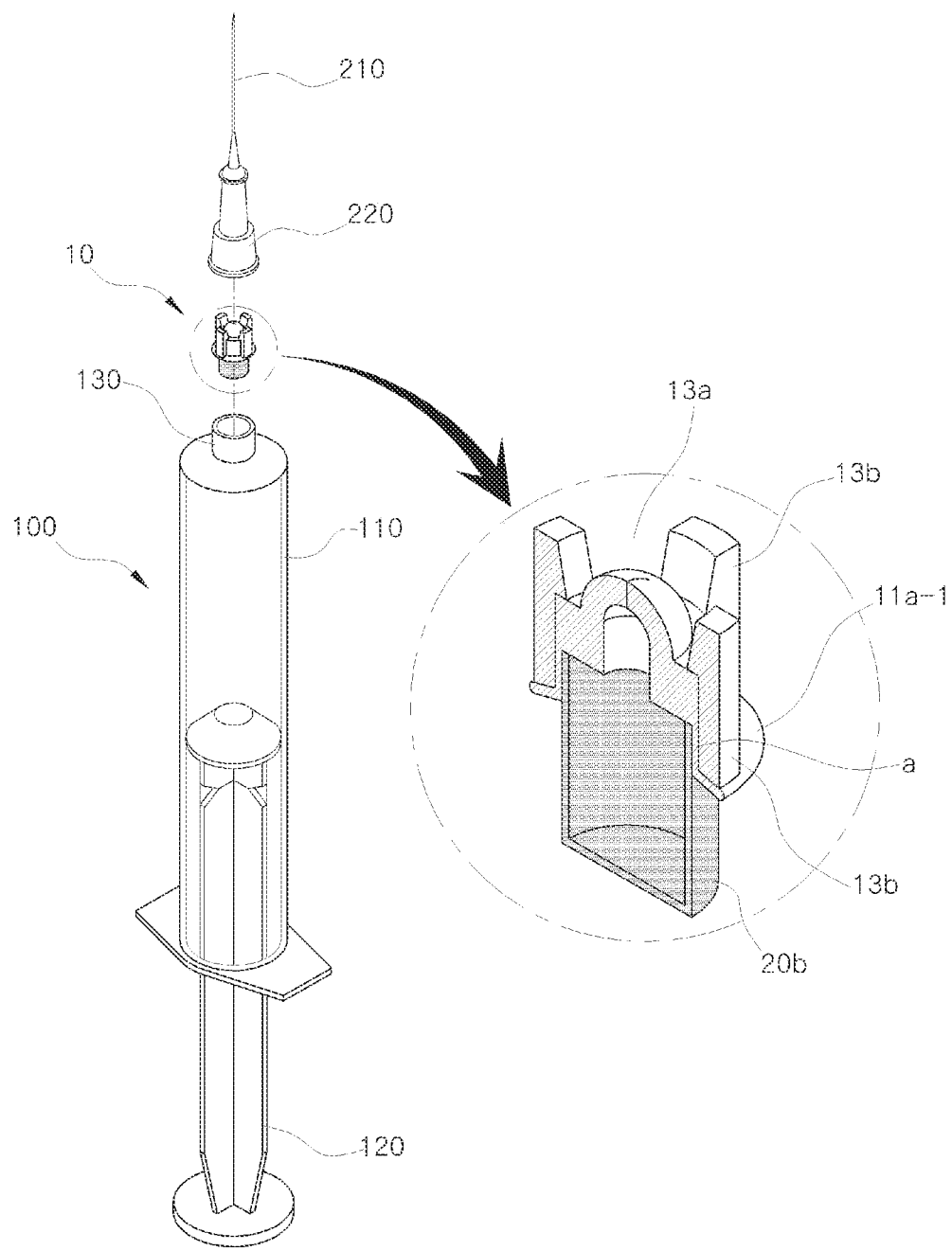
FIG. 18 is a perspective view showing a filter structure having an opened inlet path according to a second embodiment of the present invention.
Figure 19:
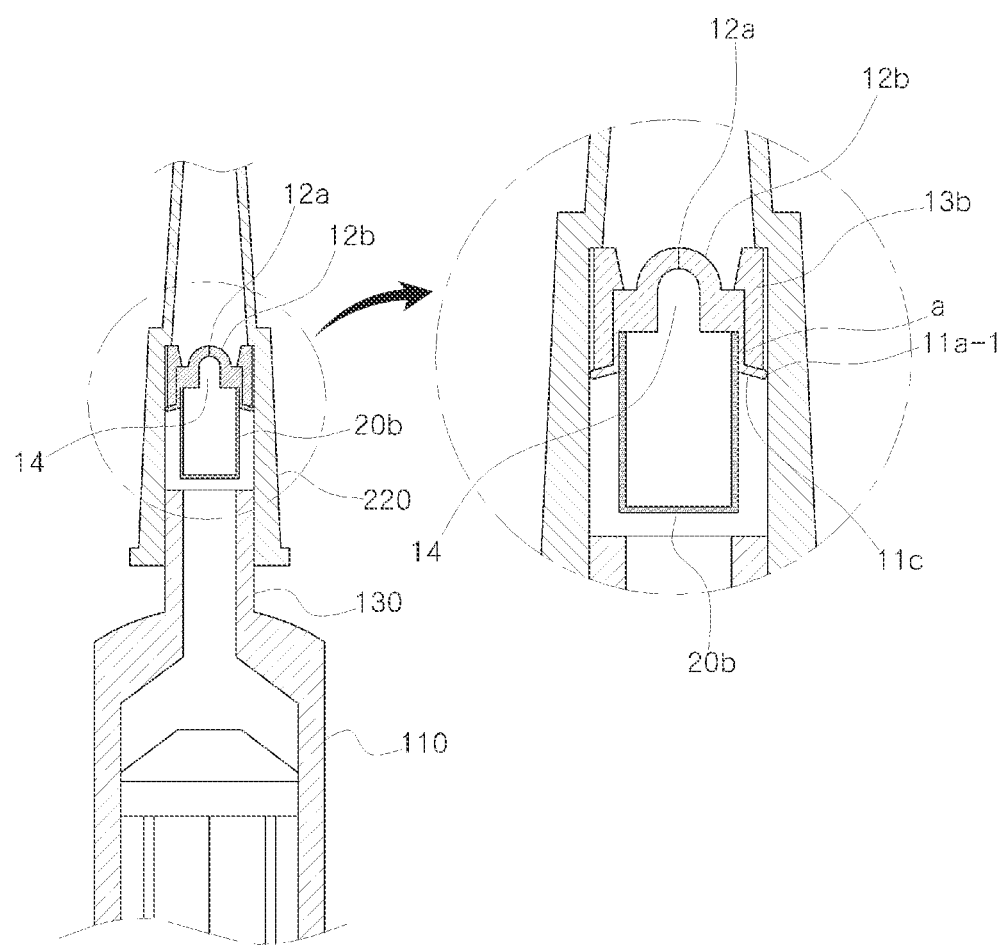
FIG. 19 is a sectional view showing a state that the filter structure of FIG. 18 is installed to a syringe.
Figure 20:
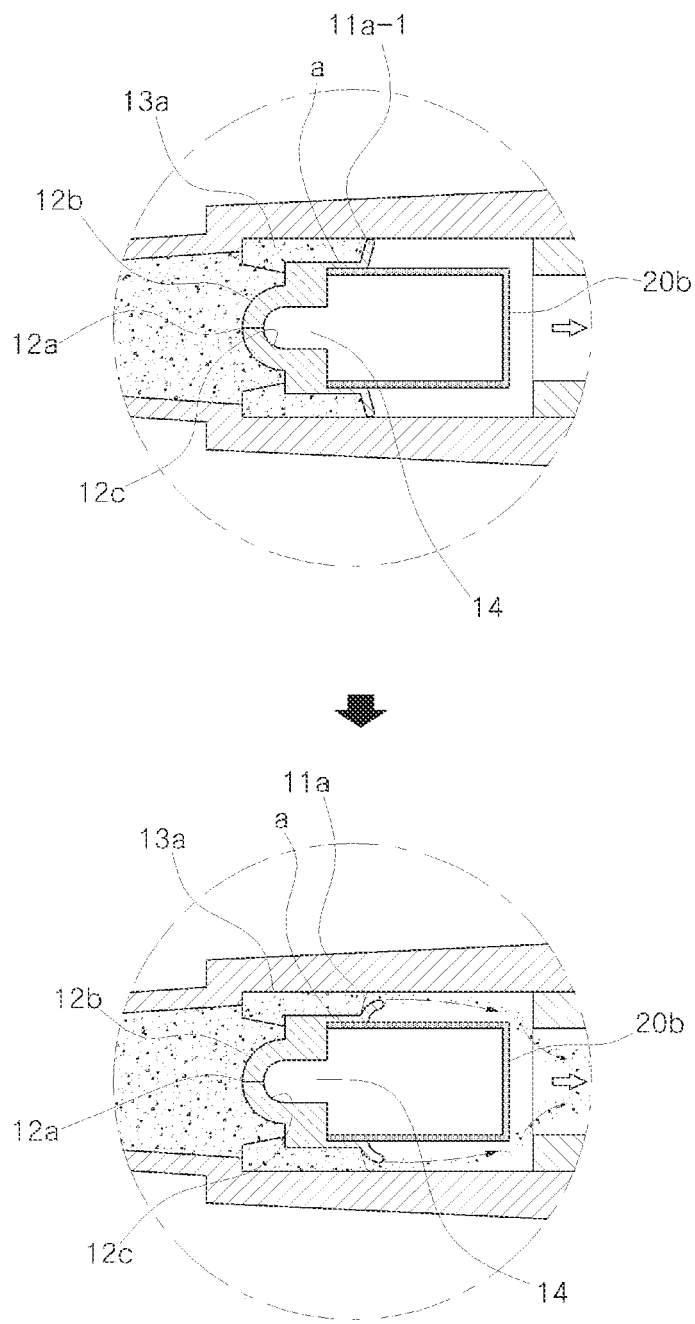
FIG. 20 is a view showing a state that a medicament liquid flows into an inlet path of the filter structure of FIG. 18.
Figure 21:
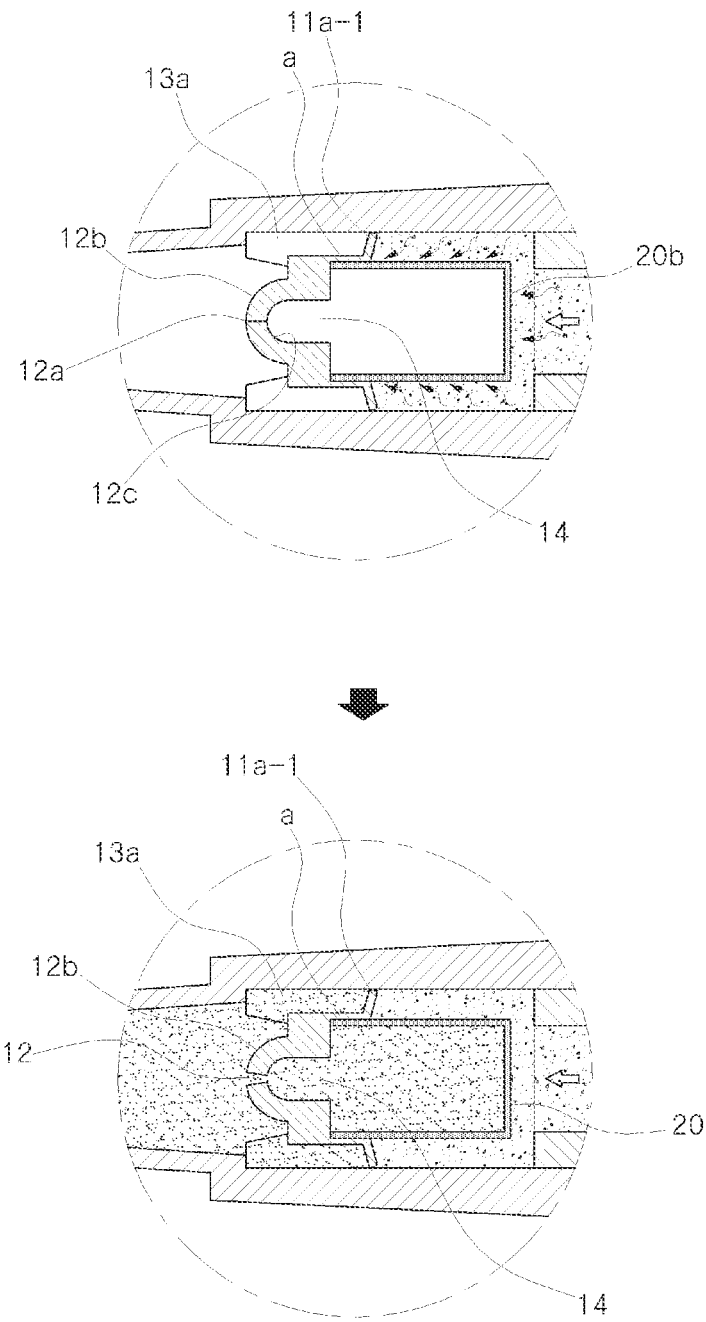
FIG. 21 is a view showing a state that a medicament liquid is exhausted through an outlet path of the filter structure of FIG. 18.
Figure 22:
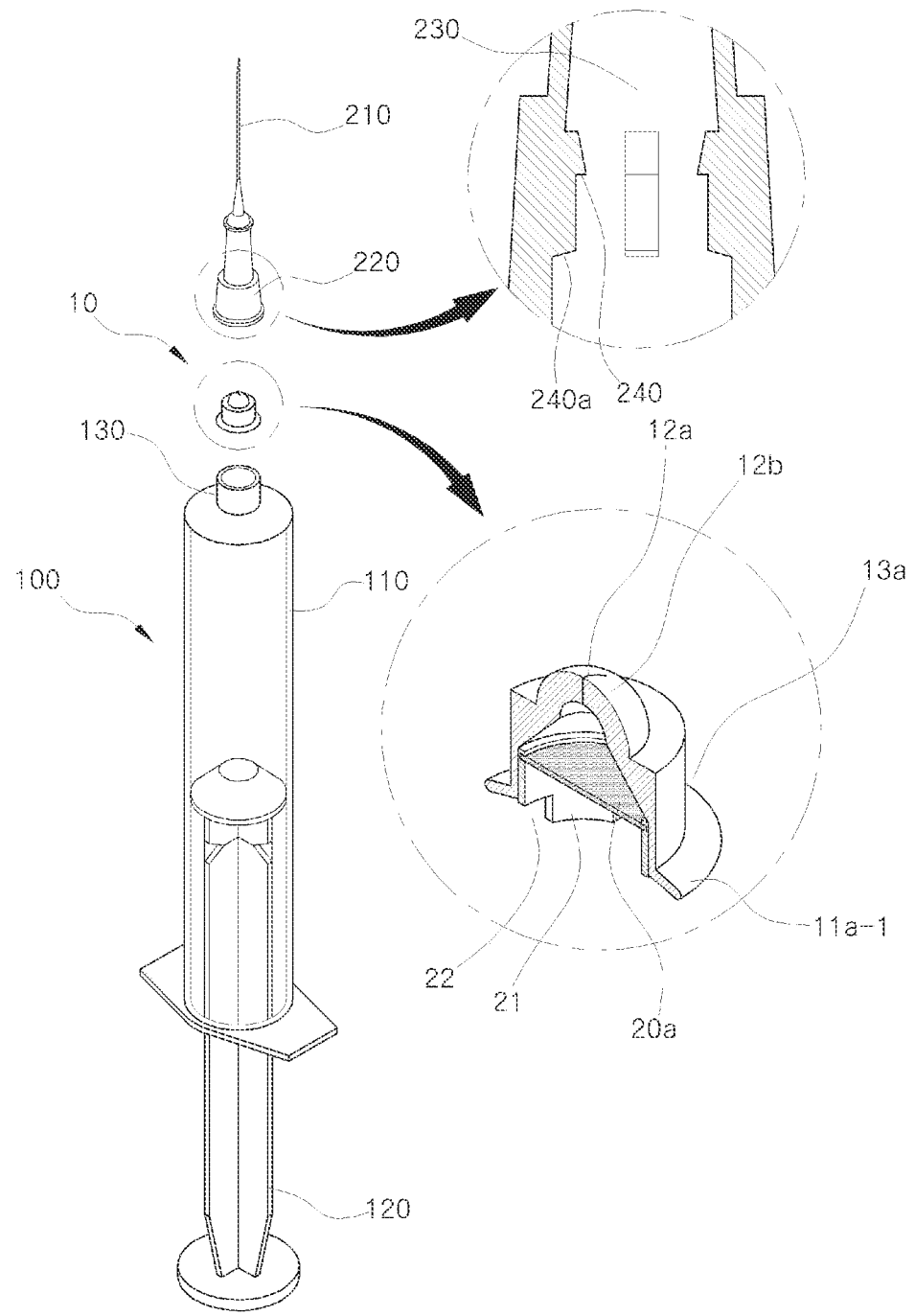
FIG. 22 is a perspective view showing a filter structure having an opened inlet path according to a third embodiment of the present invention.
Figure 23:
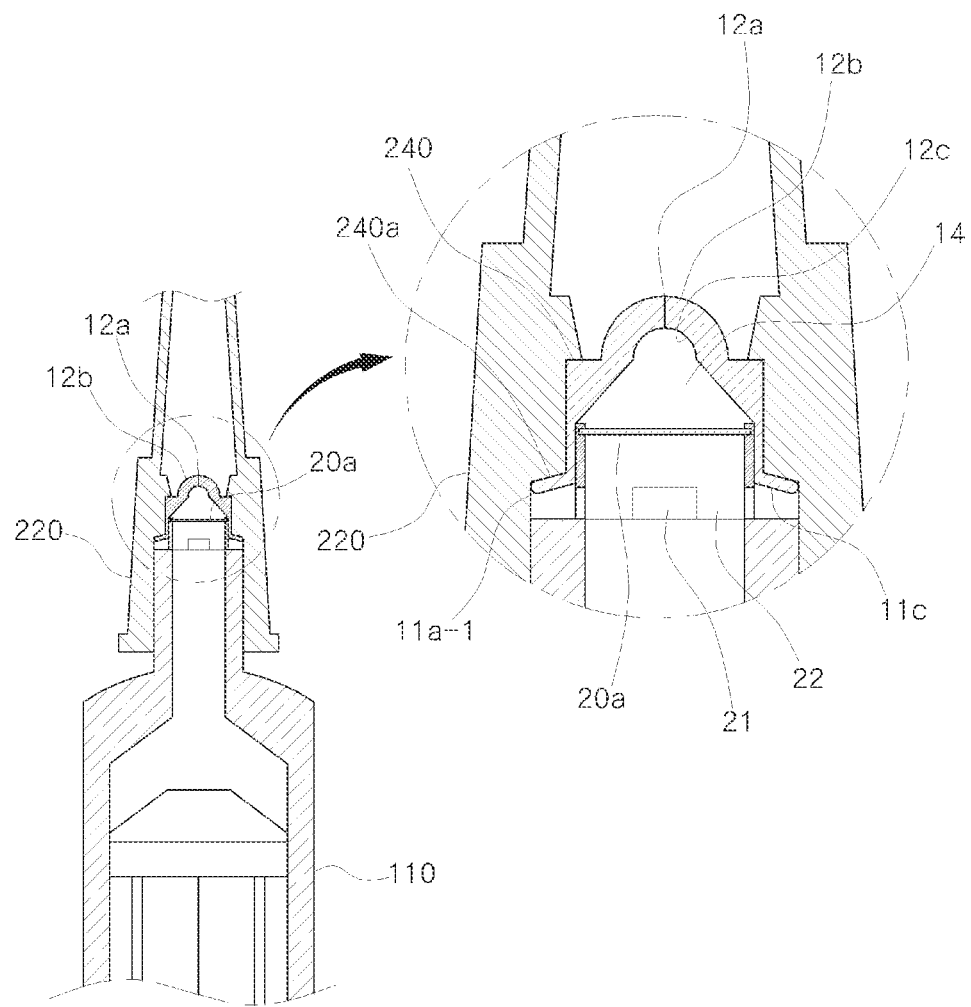
FIG. 23 is a sectional view showing a state that the filter structure of FIG. 22 is installed to a syringe.
Figure 24:
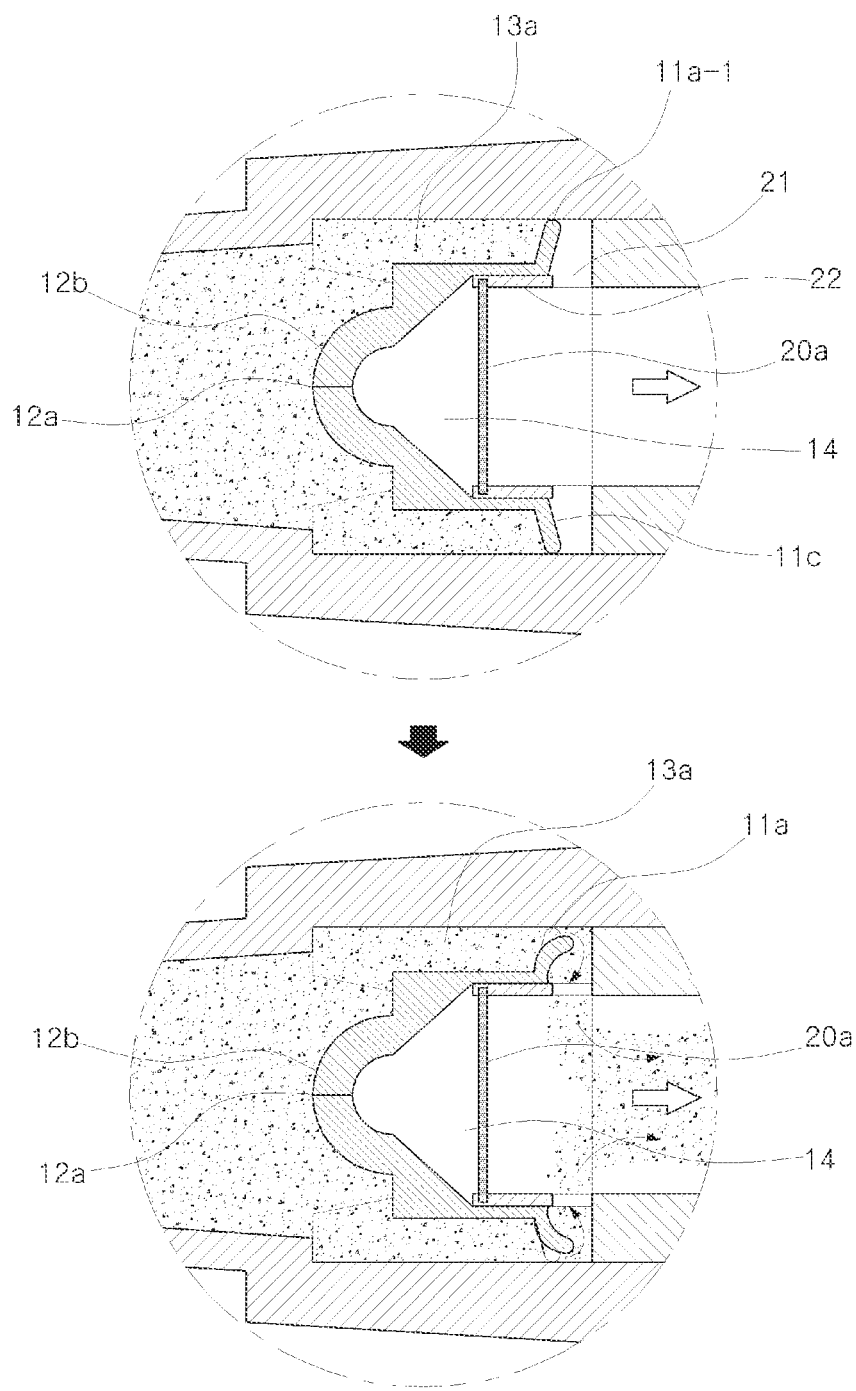
FIG. 24 is a view showing a state that a medicament liquid flows into an inlet path of the filter structure of FIG. 22.
Figure 25:
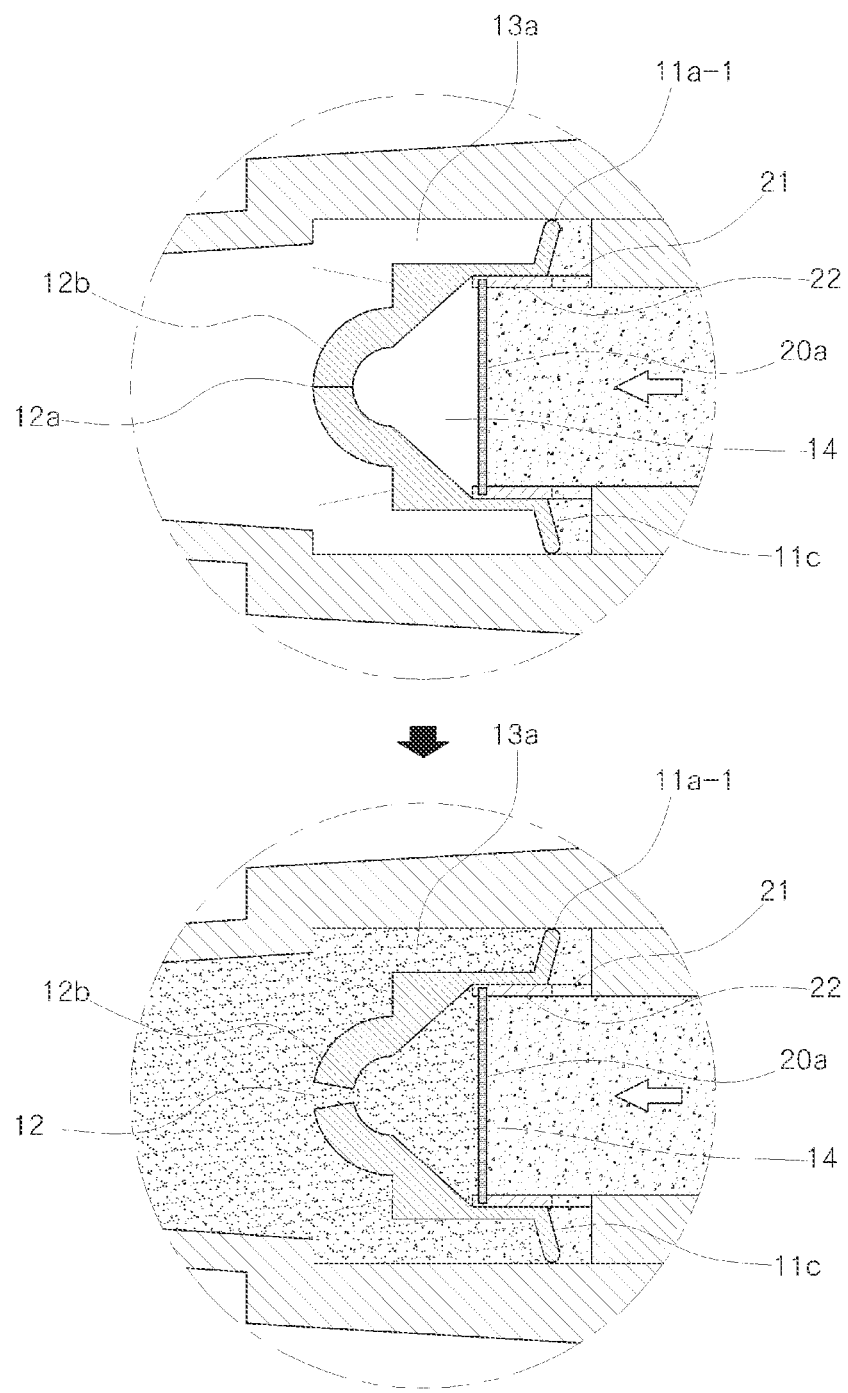
FIG. 25 is a view showing a state that a medicament liquid is exhausted through an outlet path of the filter structure of FIG. 22.
Figure 28:
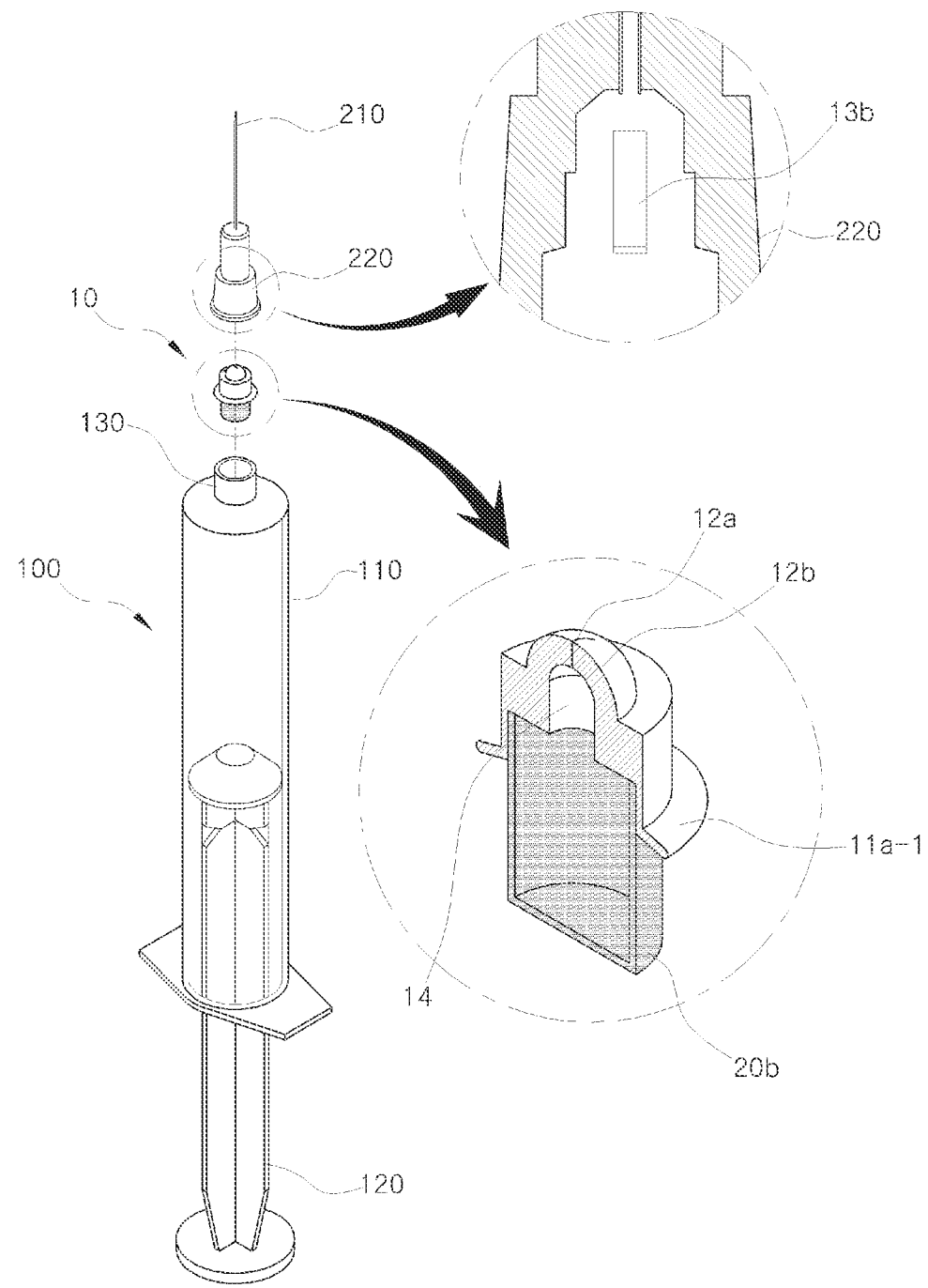
FIG. 28 is a perspective view showing a filter structure having an opened inlet path according to a fourth embodiment of the present invention.
Figure 29:
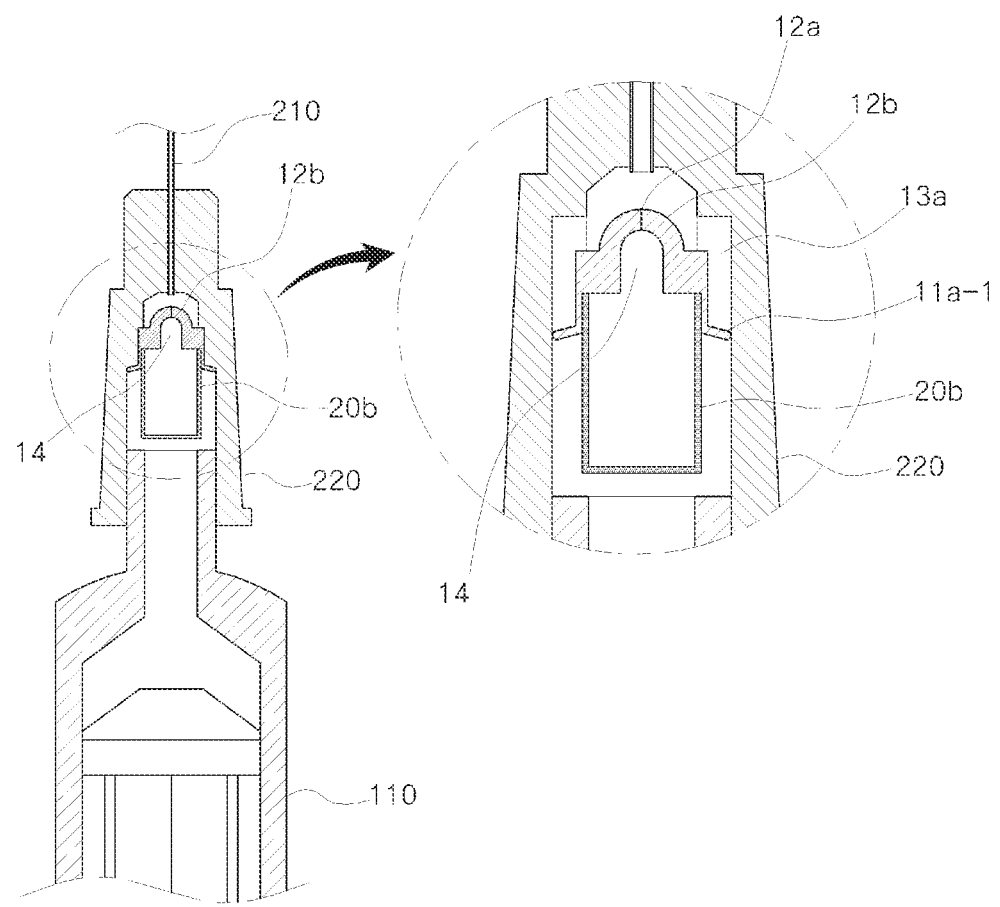
FIG. 29 is a sectional view showing a state that the filter structure of FIG. 28 is installed to a syringe.
Figure 30:
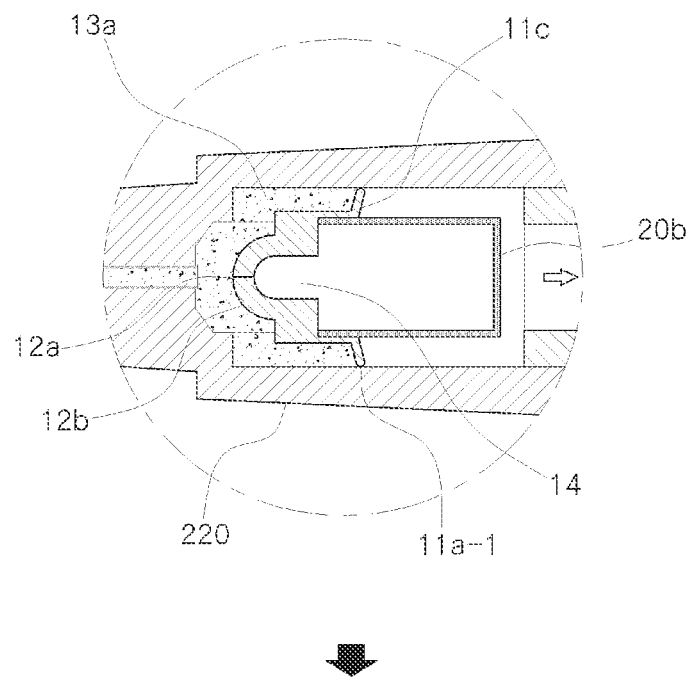
FIG. 30 is a view showing a state that a medicament liquid flows into an inlet path of the filter structure of FIG. 28.
Figure 30:
Figure 30:
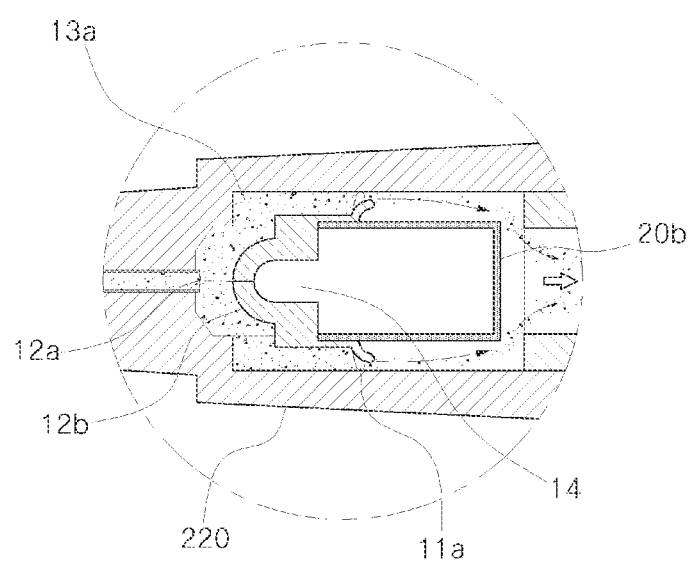

FIGS. 1, 5, and 9 are views showing filter structures having closed inlet and outlet paths independent from each other. FIGS. 1, 5 and 9 are views showing filter structures having a closed outlet path and an opened inlet path. FIGS. 13 and 18 are views showing filter structures installed in an inner space of a fixing member of a previous syringe needle to have a closed inlet path. FIGS. 22 and 28 are views showing states that a simplified filter structure is installed to the guide groove formed on the inner wall of forming the inner space of the fixing member of the previous syringe needle so that a closed inlet path is formed. FIG. 8 is a view showing an inner wall for forming the closed inlet path by coupling the filter structure to the inner wall of forming the inner space of the fixing member according to another embodiment.

In addition, FIGS. 1 and 5 show the outlet path 14 formed at the center of the filter structure 10 and the inlet path 13 formed at a curved periphery of the outlet path 14. The filter structure 10 depicted in FIG. 3 has the inlet and outlet paths 13 and 14 formed on the same plane and concentrated to one side.

Hereinafter, the structures of the filter structures according to various embodiments will be described in detail.

The filter structure 10 of FIGS. 1 and 5 has the closed outlet path 14 formed at the center and the inlet path 13 formed the curved periphery of the closed outlet path 14. The inlet path 13 has an inner diameter relatively less than that of the outlet path 14. The plurality of inlet paths 13 is independent from each other in a closed state. In this case, the inlet paths 13 are spaced apart from each other by a uniform interval if possible, so that, when a medicament liquid is sucked into the syringe body 100, the pressure generated in the inflow of the medicament liquid becomes uniform, so the medicament liquid is sucked easily and fully without any residual liquid.

In addition, the inlet and outlet paths 13 and 14 has a predetermined depth, and the inlet 11 and the outlet 12 having the check valve function are formed at the rear ends of the inlet and outlet paths 13 and 14. Due to the length of the predetermined depth, in the state that the filter structure 10 is installed in the inner space 230 of the fixing member 220 of the syringe needle 200, the filter structure 10 does not move, so that the position of the filter structure 10 is not changed (twisted) even by the pressure generated when the medicament liquid flows into and out from the syringe body 100.

In addition, the structures of the inlet 11 and the outlet 12 are symmetrical to each other, arranged on mutually opposite sides, and have the check valve function.

In order to implement the check valve function in a simple structure according to the present invention, the inlet 11 and the outlet 12 are formed at the rear ends of the inlet path 13 and the outlet path 14 having the predetermined depths. The inlet 11 and the outlet 12 are formed in a film type having a predetermined thickness. The inlet 11 and the outlet 12 of the film type have cut lines 11a and 12a such that the inlet 11 and the outlet 12 are maintained in a closed state at ordinary times due to elasticity of the films and are opened through the cut lines 11a and 12a due to the pressures.

The inlet 11 and the outlet 12 of the film type having the cut lines 11a and 12a have inner curved surfaces 11c and 12c curved in exhausting directions of the medicament liquid through the inlet 11 or the outlet 12 to concentrate the medicament liquid, so that the cut lines 11a and 12a are easily opened by instantaneous pressures, so the medicament liquid is easily exhausted. Protruded curved surfaces 11b and 12b are formed at opposite sides of the inner curved surfaces 11c and 12c to receive low pressures, so that the medicament liquid is gathered only to either the inlet path 13 or the outlet path 14 which is selected by inflow or outflow, so the check valve function is enhanced and easily implemented and in addition, the inlet 11 and the outlet 12 are enabled to be opened by even a low pressure.

Figure 2:
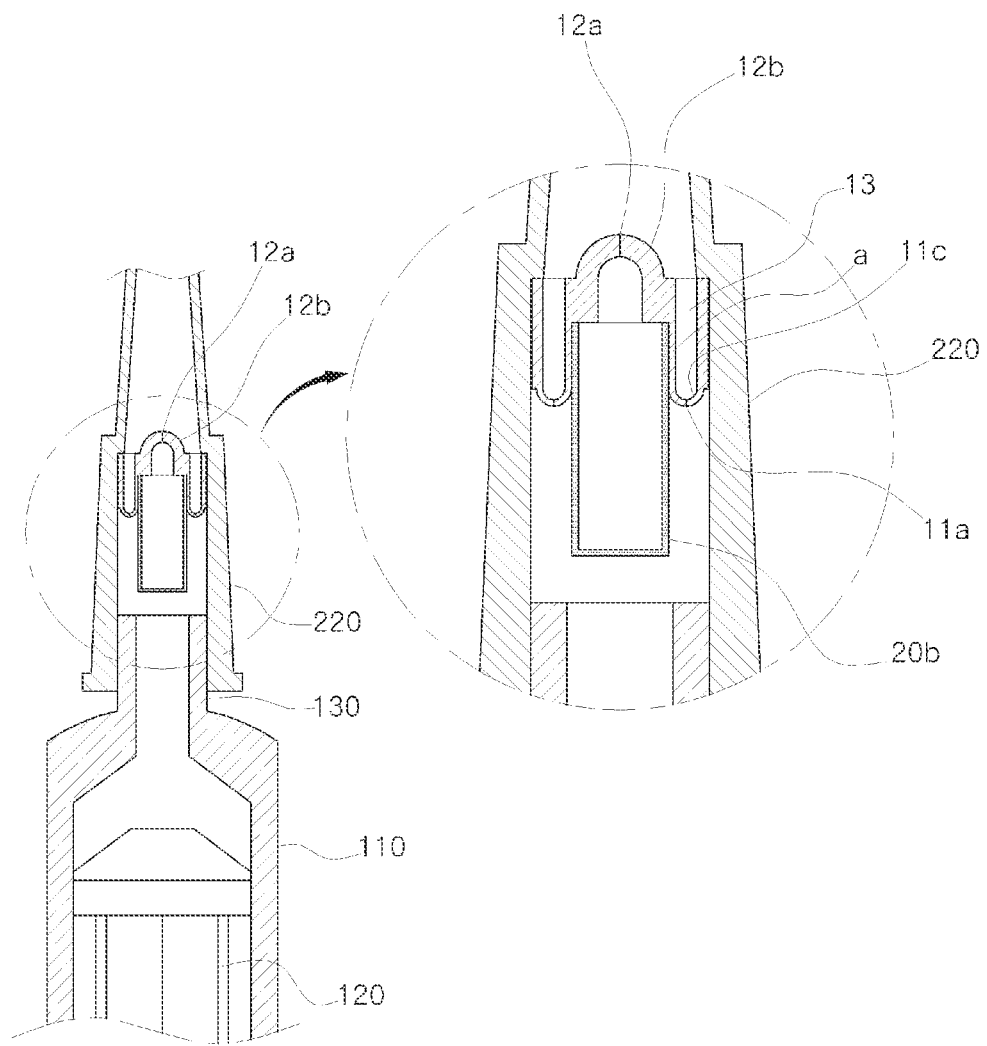
FIG. 2 is a sectional view showing a state that the filter structure of FIG. 1 is installed to a syringe.
Figure 3:
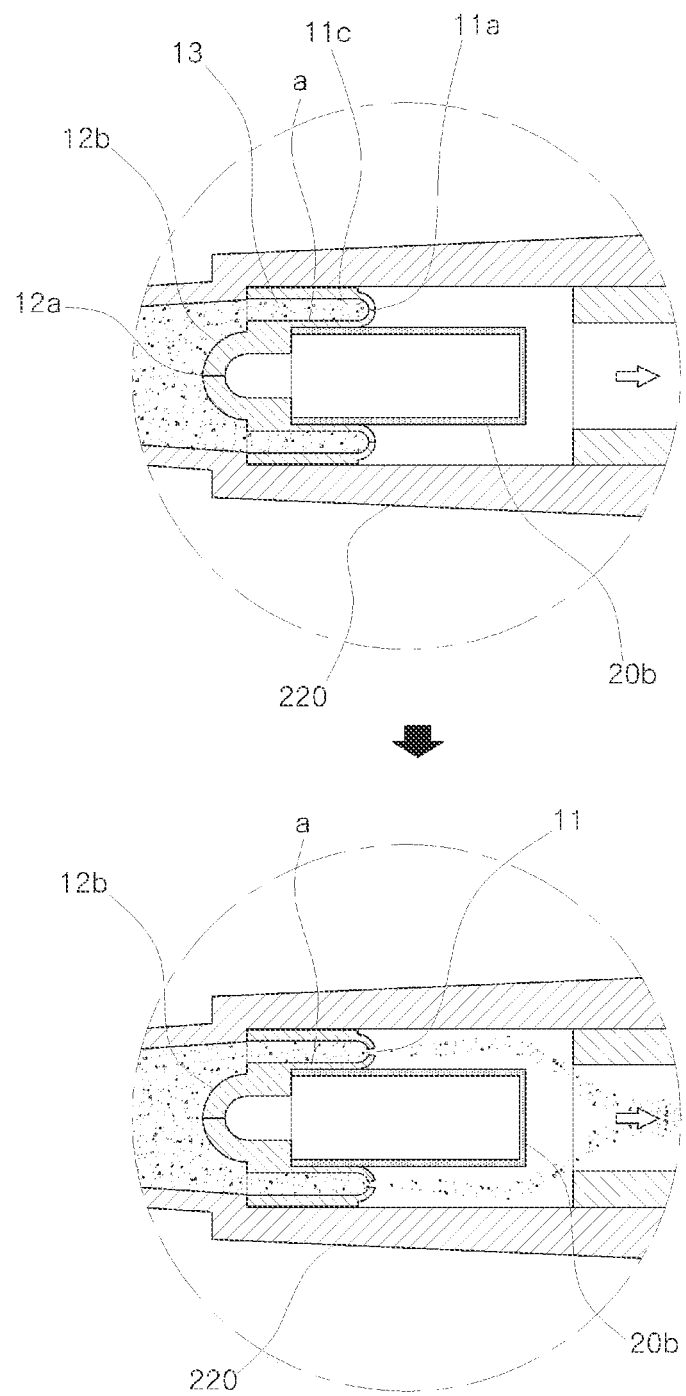
FIG. 3 is a view showing a state that a medicament liquid flows into an inlet path of the filter structure of FIG. 1.
Figure 4:
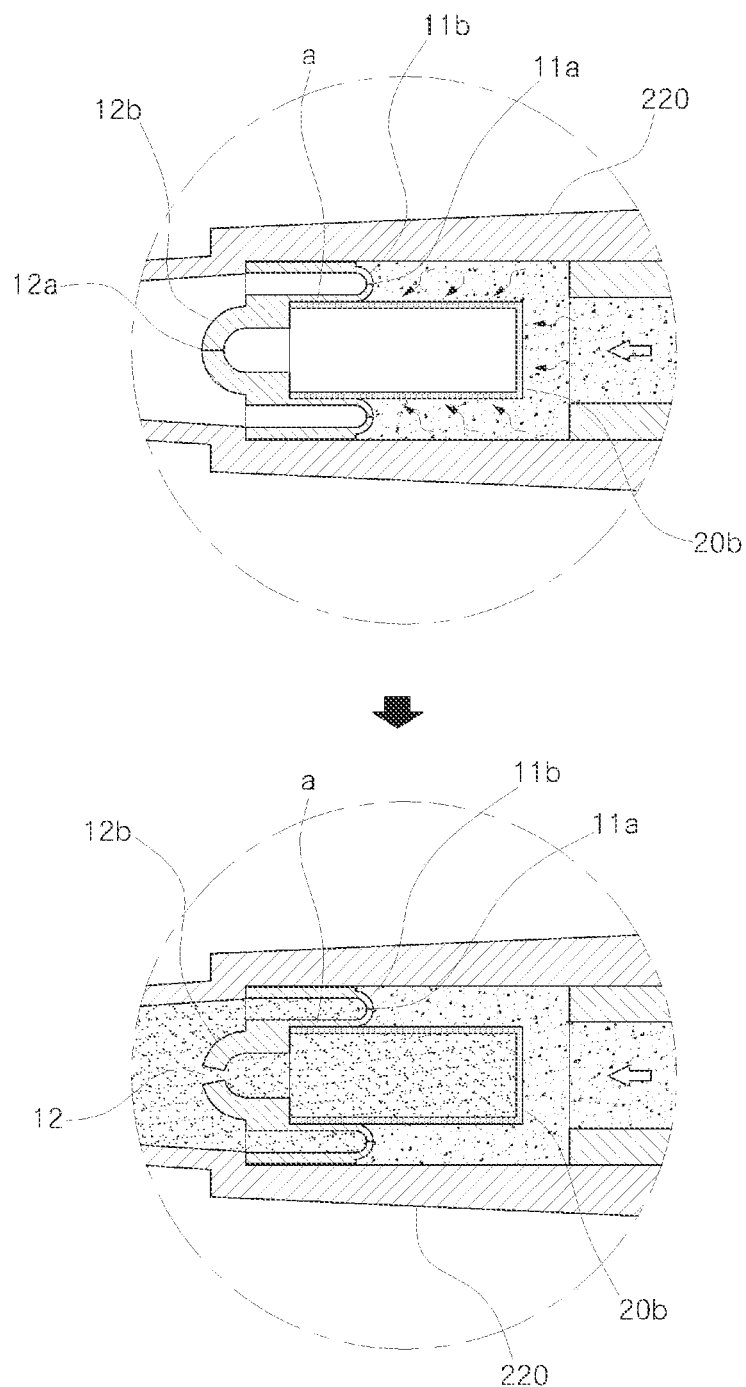
FIG. 4 is a view showing a state that a medicament liquid is exhausted through an outlet path of the filter structure of FIG. 1.

In addition, as shown in FIGS. 1 and 2, the protruded curved surface 12b protruded toward the outside of the outlet 12 of the outlet path 14 is protruded from the center of the fixing member 220 of the syringe needle 200, so that the medicament liquid is introduced into the inlet path 13 while being naturally dispersed to an outside due to the protruded curved surface 12b when the medicament liquid is sucked from an ampoule into the syringe body 100. As shown in FIGS. 4 and 8, the protruded curved surface 11b protruded toward the outside of the inlet 11 of the inlet path 13, so that the medicament liquid is fully exhausted while being naturally dispersed to the outlet path 14 when the medicament liquid is injected into a patient.

As shown in FIG. 5, the filter 20, which is used to filter impurities when a medicament liquid is injected into a patient by exhausting the medicament liquid through the outlet 12, may be formed in a plane 20a shape or in a hollow tube body 20b depicted FIG. 1 which is not modified or torn due to the pressure generated in injection. A means may be used to allow the filter 20 to be latched at a predetermined position of the outlet path 14, but may be variously modified in the scope of the objects of the present invention.

When the filter 20 is formed in the tube body 20b, the protruded tube body is tightly closed to the front end of the syringe body 100, the filter structure is supported without being sucked when the medicament liquid is sucked. When the filter 20 is formed in the plane shape 20a, the plane filter 20a is fixed by a partition wall 21 made of a solid material such that the plane filter 20a is prevented from being twisted. The partition wall 21 extends rearward perpendicularly to the rim of the plane filter 20a, so that the partition wall 21 protrudes rearward and is support without being sucked by the front end 130 of the syringe body.

As shown in FIGS. 13 and 22, the partition wall 21 described below has an opening 22 such that the medicament liquid is easily sucked. The partition wall 21 reinforces a thin portion a of forming a boundary between the inlet path 13 and the outlet path 14 of the filter structure 10.

However, when the filter 20 is prepared in the form of a plane plate 20a, a bottle neck phenomenon occurs so that the pressure is increased. To the contrary, when the filter 20 is prepared in the form of a tubular body 20b having a hollow inner space, the pressure is dispersed so that the injection is performed at a low pressure during the injection to a patient.

However, when the openings 22 are formed on the partition wall 21 for fixing the filter 20a by a predetermined depth and a predetermined interval, the bottle neck phenomenon is relieved even if the filter 20a is the plane filter 20a, so that the injection pressure is reduced.

In addition, the filter structure 10 of FIG. 9 (as well as FIGS. 10 to 12) is integrally formed similarly to that of FIGS. 1 and 5, but the inlet path 13 and the outlet path 14 of the filter structure 10 of FIG. 9 are concentrated to one side, so that it is difficult to allow a medicament liquid to fully flow into the inlet path 13 or exhaust out of the outlet path 14 when the medicament liquid flows into the inlet path 13 or exhausts out of the outlet path 14. Although the filter structure 10 has a portion requiring a higher pressure, the cut lines 11a and 12a formed in the inlet 11 and the outlet 12, the inner curved surfaces 11c and 12c formed on the inside of the inlet 11 and the outlet 12, and the protruded curved surfaces 11b and 12b formed on the outside of the inlet 11 and the outlet 12 simply implement the check valve function of the inlet 11 and the outlet 12. In addition, since each of the inlet path 13 and the outlet path 14 has a predetermined depth, the location of the filter structure 10 installed in the inner space 230 of the fixing member 220 of the syringe needle 200 is not changed (twisted) even when a pressure is generated by the inflow and outflow of the medicament liquid and the injection can be performed while filtering impurities without exchanging the syringe needle 200, so that the objects of the present invention can be effectively achieved.

FIGS. 13, 18, 22, and 28 are views showing an opened inlet path 13a as the inlet path of the filter structure 10. A closed inlet path may be implemented by installing the filter structure 10 having the open inlet path to the fixing member 220 of a previous syringe needle 220. The filter structures of the FIGS. 13 and 18, which are installed in the inner space of the fixing member of a previous syringe needle, are implemented in a close type. The filter structures of FIGS. 22 and 28 are respectively installed on the inner wall which forms the inner space of the fixing member of a previous syringe needle and of which the structure is modified.

As shown in FIGS. 13 and 18, the closed outlet path 14 is formed at the center of the filter structure 10 having the opened inlet path and the opened inlet path 13a is formed at the periphery the closed outlet path 14. The opened inlet path 13a is tightly closed to the inner wall 230a of the inner space 230 of the fixing member 220 of the syringe needle 220, so that the opened inlet path 13a is closed. In this case, the opened inlet path 13a includes a plurality of opened inlet paths which are independent from each other and formed by pillars 13b protruding toward the outer wall of the closed outlet path 14 by a predetermined interval and having a predetermined thickness. At this time, the pillars 13b are formed to have the regular interval such that the open inlet paths 113a can be kept at the uniform interval, so the pressure generated when the liquid is introduced may be uniform, so that the liquid can be easily introduced.

Further, the pillars 13b of forming the opened inlet path 13a and the closed outlet path 14 have a predetermined depth and the inlet 11a and the outlet 12 having the check valve function are formed on the ends of the pillar 13b and the closed outlet path 14. Since the pillars 13b of forming the opened inlet path 13a and the closed outlet path 14 have the predetermined depth, in the state that the filter structure 10 is installed in the inner space 230 of the fixing member 220 of the syringe needle 200, the location is prevented from being changed by the pressure generated when a medicament liquid flows in or out.

Further, according to the present invention, in order to implement the inlet 11a of the opened inlet path 13a and the outlet 12 of the closed outlet path having the check valve function in a simple structure, an inclined film 11a-1 is formed at a rear end of the opened inlet path 13a and the pillar 13a is formed on an upper surface of the inclined film 11a-1, so that the inclined film 11a-1 is folded to only one side to perform the check valve function. In addition, the pillar 13b is supported in the inner space 230 of the fixing member 220 of the syringe needle 200 so that a medical liquid easily flows into the syringe needle 200 while the inclined film 11a-1 is easily opened when the medical liquid is input through the opened inlet path 13a. When the medicament liquid flows out through the closed outlet path 14, the check valve function of allowing the medicament liquid to flow in one-way direction is perfectly performed by an inclined angle of the inclined film 11a-1 and the pillar 13b.

According to the present invention, a width of the inclined film 11a-1 protruding toward an outside is longer than a thickness of the pillar 13b, so that the inclined film 11a-1 is easily opened when a medicament liquid flows therein.

However, the pillar 13b has a thickness equal to a width of the inclined film 11a-1 according to a material characteristic and the inclined film 11a-1 is folded at only a portion in which the pillar 13b is not formed, so that the medicament liquid easily flows therein.

As shown in FIGS. 1, 5, and 9, the outlet 12 formed at the rear end of the outlet path 14 is formed in a shape of a film having a predetermined thickness. The film is prepared in the form of a cut line 12a, which is opened by the pressure, and the film in the form of the cut line 12a allows the outlet 12 to have the inner curved surface 12c, which is curved in an exhausting (progressing) direction of the medicament liquid, so that the cut line 12a is easily opened and the exhaustion is facilitated. In addition, the film in the form of the cut line 12a allows the outlet 12 to have the protruded curved surface 12b opposite to the inner curved surface 12c such that less pressure is applied thereto. Thus, the medicament liquid is primarily concentrated to the opened inlet path 13a and the outlet path 14 during injection and exhaustion, so the check valve function is enhanced and the pressure is reduced.

In addition, as shown in FIGS. 15, 16, 20, and 21, the protruded curved surface 12b protruded to an outside of the outlet 12 of the outlet path 14 is placed at the center of the fixing member 220 of the syringe needle 200, so that the medicament liquid is naturally dispersed to an outside due to the protruded curved surface 12b when the medicament liquid is sucked into the syringe body 100, so the medicament liquid is input to the opened inlet path 13a. As shown in FIGS. 15, 16, 20, and 21, when the medicament liquid flows into the opened inlet path 13a, the inclined film 11a-1 is folded to the inside. Then, when the medicament liquid is injected to a patient, while the inclined film 11a-1 is opened to the outside, the medicament liquid is naturally concentrated onto the closed outlet path 14 due to the inclined film 11a-2, so that the medicament liquid is fully exhausted.

As shown in FIG. 13, the filter 20, which is used to filter impurities when a medicament liquid is injected into a patient by exhausting the medicament liquid through the outlet 12, may be prepared in the form of a plane filter 20a as depicted in FIG. 13 or a hollow tubular body 20b as depicted in FIG. 18. The filter 18 is not deformed or torn even if the pressure is applied thereto during the injection. A device may be used to allow the filter 20 to be latched at a predetermined position of the outlet path 14, and the above elements may be variously modified within the scope of the objects of the present invention.

However, when the filter 20 is prepared in the form of the plane filter 20a, a bottle neck phenomenon occurs so that the pressure is increased. To the contrary, when the filter 20 is prepared in the form of the tubular body 20b, the pressure is dispersed so that the injection is performed at a low pressure during the injection to a patient.

As shown in FIG. 13, the partition wall 21 for fixing the plane filter 20a has the opening 22 such that the medicament liquid is easily sucked. The partition wall 21 reinforces a thin portion a of forming a boundary between the inlet path 13 and the outlet path 14 of the filter structure 10. When the openings 22 are formed on the partition wall 21 for fixing the filter 20a by a predetermined depth and a predetermined interval, the bottle neck phenomenon is relieved even if the filter 20a is the plane filter 20a, so that the injection pressure is reduced similarly with the case in which the filter is the tubular filter 20b as shown in FIG. 5.

Figure 26:
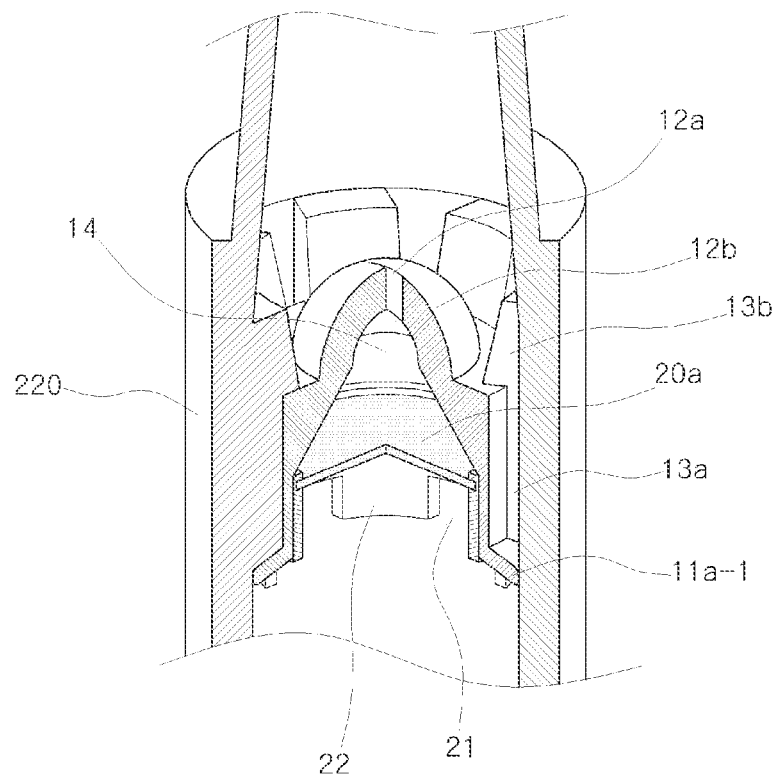
FIG. 26 is a sectional view showing a state the filter assembly of FIG. 22 is installed in an inner space of a fixing member.
Figure 27:
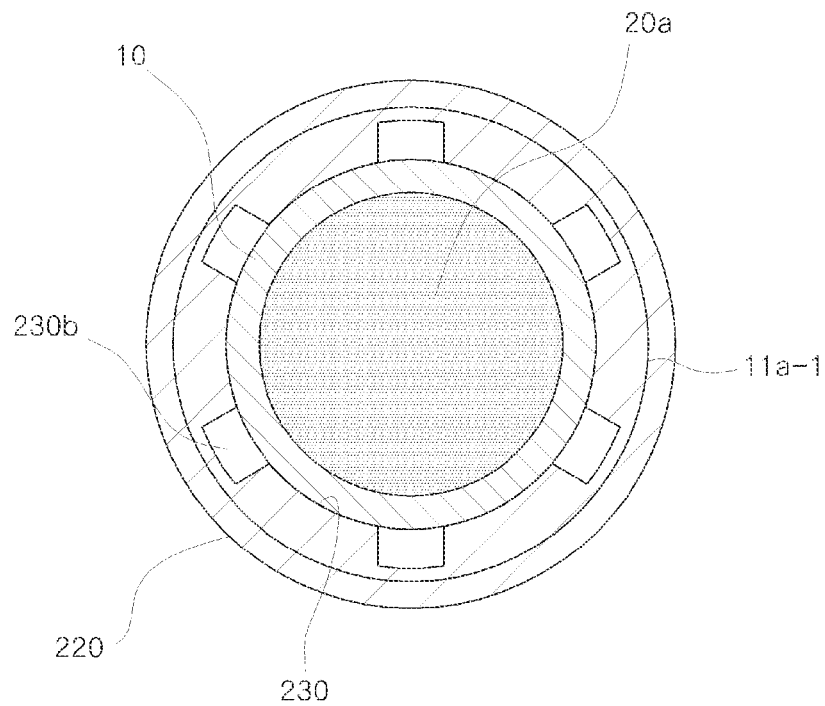
FIG. 27 is a sectional view showing a guide groove formed on the inner wall of FIG. 22.

FIGS. 22 and 28 are views showing a filter structure 10 which is installed in the inner wall 230a which is modified in the structure and in which the inner space 230 of the fixing member 220 of the previous syringe needle 200, so that the filter structure 10 is simplified and the inflow pressure is reduced. The filter structure 10 includes the closed outlet path 14 formed at the center thereof, the outlet 12 having the check valve function at the rear end of the outlet path 14, and the opened inlet path 13a formed on the curved periphery. As shown in FIGS. 26 and 27, the opened inlet path 13a is closely installed to the inner wall 230 which forms the inner space 230 of the fixing member 220 of the syringe needle 200, so that the closed inlet path is formed by the guide groove 230b formed on the inner wall.

To this end, the guide groove 230b is vertically formed on the inner wall 230a of forming the inner space 230 of the fixing member 220 at a predetermined depth, so that the opened inlet path 13a is converted into the closed inlet path by the guide groove 230b.

If possible, the guide grooves 230b are formed to have the predetermined depth and the predetermined interval in such a manner that the pressure, which is generated when a medicament liquid flows into the syringe body 100 in a state that the closed inlet path is formed, is uniformly formed so that the injection is facilitated.

In addition, the inner wall 230a, in which the guide groove 230b is formed and the inner space of the fixing member 220 of the filter structure of forming the opened inlet path 13a is formed the inner space, is tightly closed to the outer wall of the filter structure 10, so that the closed inlet path is formed. The guide groove 230b is formed while passing through the step protrusions 240 and 240a formed in the inner wall of forming the inner space of the fixing member, and the inlet 11a having the check valve function is formed to be operated in only inflow while the top surface of the inclined film 11a-1 is being latched to the low end of the step protrusion 240a.

In addition, since the guide groove 230b and the outlet path 14, which convert the opened inlet path 13a into the closed inlet path, has the predetermined depth, the location of the filter structure 10 installed in the inner space 230 of the fixing member 220 of the syringe needle 200 is not changed even when a pressure is generated by the injection and exhaustion of the medicament liquid.

Further, according to the present invention, in order to implement the inlet 11*a* of the opened inlet path 13*a* and the outlet 12 of the closed outlet path having the check valve function in a simple structure, an inclined film 11*a*-1 protrudes from a rear end of the opened inlet path 13*a* in an annular rim shape and the upper surface of the inclined film 11*a*-1 is supported by the low end, that is, the step protrusion 240*a* of the guide groove 13*c* introduced into the inner wall 230*a* that forms the inner space 230 of the fixing member 220 and an upper surface of the inclined film 11*a*-1, so that the inclined film 11*a*-1 is folded to only one side to perform the check valve function. At the same time, the inclined film 11*a*-1 is supported at the low end of the stop protrusion 240*a* of the guide groove 230*b* formed in the inner wall 230*a* of the inner space of the fixing member 220 of the syringe needle 200, so that so the medicament liquid easily flows in the syringe body while the inclined film 11*a*-1 is being smoothly folded when a medicament liquid flows in the syringe body.

When the medicament liquid flows out through the closed outlet path 14, the check valve function of allowing the medicament liquid to flow in one-way direction is perfectly performed as an inclined angle of the inclined film 11*a*-1 is compactly supported at the low end (step protrusion 240*a*) of the guide groove 230*b*.

According to the present invention, the width of the inclined film 11*a*-1 supported by the low end of the guide groove 230*b* is suitably adjusted by taking into consideration the pressure generated when the medicament is exhausted.

However, since the width support varies according to a hardness of a material, the width may be variously changed within the scope of the present invention.

As shown in FIGS. 1, 5, 9, 13, 18, and 22, the outlet 12 formed at the rear end of the outlet path 14 is formed in a shape of a film having a predetermined thickness. The film is prepared in the form of a cut line 12*a*, which is opened by the pressure, and the film in the form of the cut line 12*a* allows the outlet 12 to be curved in an exhausting (progressing) direction of the medicament liquid, so that the cut line 12*a* is easily opened due to the concentration of pressure and the exhaustion is facilitated. In addition, the film in the form of the cut line 12*a* allows the outlet 12 to have the protruded curved surface 12*b* opposite to the inner curved surface such that less pressure is applied thereto. Thus, the medicament liquid is primarily concentrated to the opened inlet path 13*a* during injection, so the check valve function is enhanced and the pressure is reduced.

Figure 31:
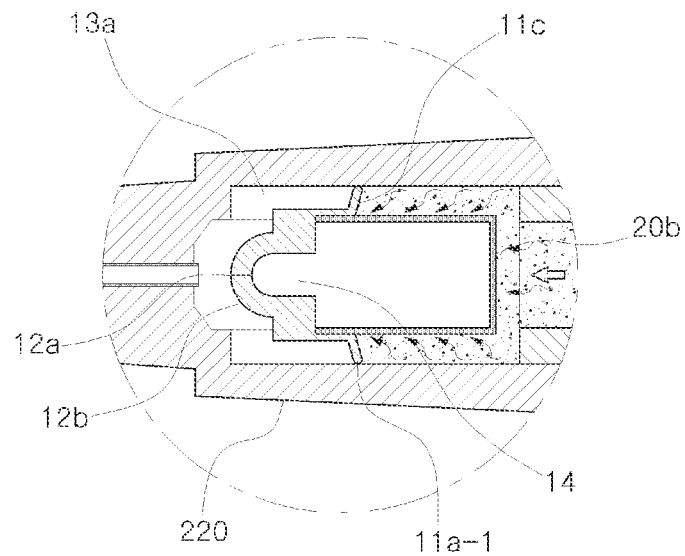
FIG. 31 is a view showing a state that a medicament liquid is exhausted through an outlet path of the filter structure of FIG. 28.
Figure 31:
Figure 31:
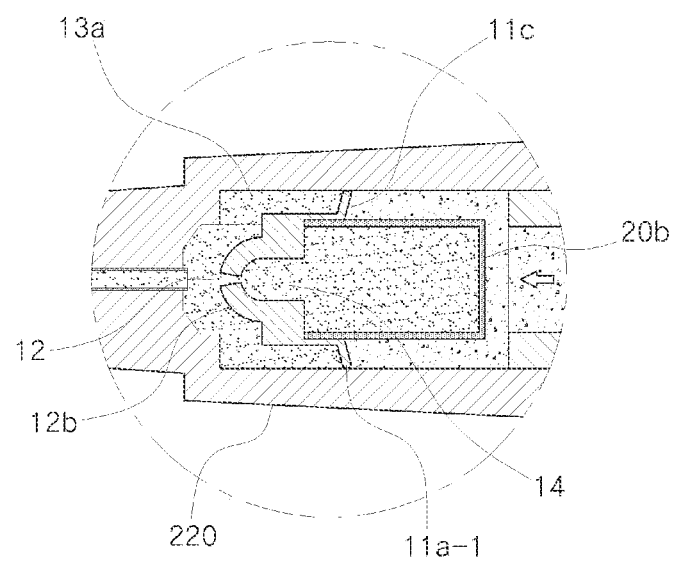
Figure 32:
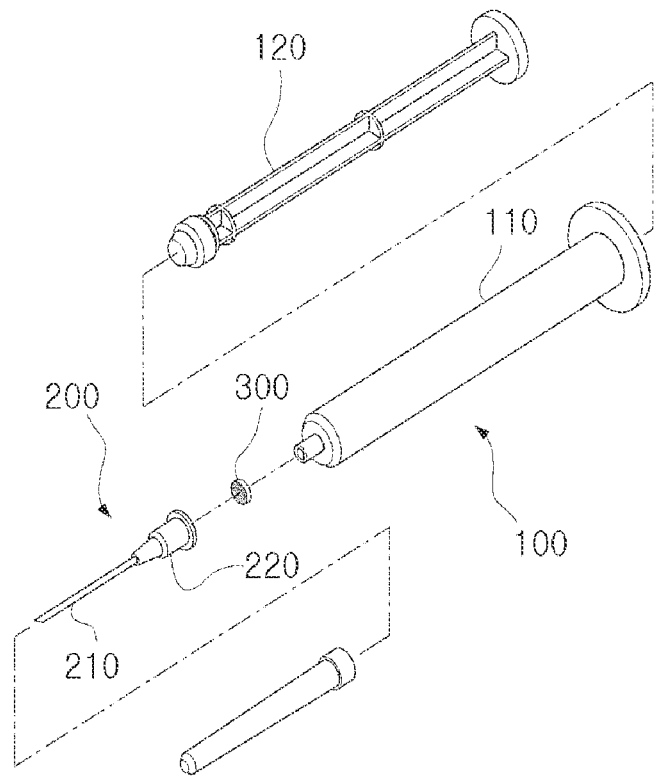
FIG. 32 is an exploded perspective view showing a state that a needle filter according to the related art is installed to a syringe.
Figure 33:
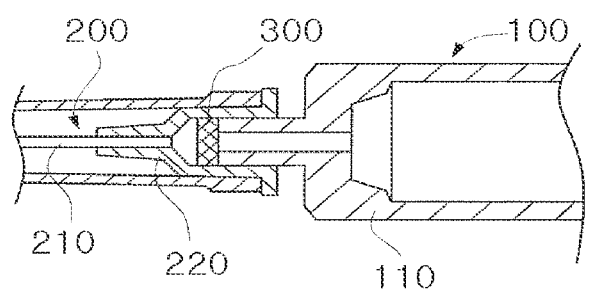
FIG. 33 is a sectional view showing an installation state of FIG. 32.

In addition, as shown in FIGS. 24, 25, 26, 30, and 31, the protruded curved surface 12*b* protruded toward the outside of the outlet 12 of the outlet path 14 is protruded from the center of the fixing member 220 of the syringe needle 200, so that the medicament liquid is introduced into the inlet path 13 while being naturally dispersed to an outside due to the protruded curved surface 12*b* when the medicament liquid is sucked from an ampoule into the syringe body 100. As shown in FIGS. 26 and 31, when the medicament liquid is injected into a patient through the inclined surface 11*c* after the medicament liquid is input while the inclined surface 11*c* is opened toward the outside of the inlet 11*a* of the opened inlet path 13*a*, the medicament liquid is fully exhausted while being naturally dispersed to the outlet path 14.

In this case, a guide groove 240*a* is formed from a step protrusion 240*a* by which a top surface of the inclined film 11*a*-1 is supported to a step protrusion 240 by which the front portion of the filter structure 10 is supported, so that the filter structure 10 is fixed without entering into an upper portion and the medicament liquid is easily introduced.

As shown in FIG. 22, the filter 20, which is used to filter impurities when a medicament liquid is injected into a patient by exhausting the medicament liquid through the outlet 12, may be formed in a plane 20*a* shape or in a hollow tube body 20*b* depicted FIG. 28 which is not modified or torn due to the pressure generated in injection. A means may be used to allow the filter 20 to be latched at a predetermined position of the outlet path 14, but may be variously modified in the scope of the objects of the present invention.

However, when the filter 20 is formed in the plane shape 20*a*, a bottle neck phenomenon occurs so that the pressure is increased. To the contrary, when the filter 20 is formed in the tube body 20*b*, the pressure is dispersed so that the injection is performed at a low pressure during the injection to a patient.

As shown in FIGS. 22 and 28, although the guide groove 230*b* is formed on the inner wall 230*a* of forming the inner space 230 of the fixing member 220 in order to form the closed inlet path based on the opened inlet path, even when a guide protrusion is substituted for the guide groove, the same effect is achieved.

The present invention is extensively applicable to fields of designing and manufacturing a medical optical treatment device to improve scalp and prevent hair loss. The present invention relates to a medical filter needle which is detachably installed to a syringe consisting of a cylinder and a piston in use in order to prevent a fine powder, which is generated from a glass or plastic ampoule, from being injected into a patient when the medicament liquid of the ampoule made of glass or plastic, which is absorbed into the cylinder of the syringe, is injected through a syringe needle, so that the safety of a patient is secured and the suction and injection are easily performed.

What is claimed is:

1. A filter needle for a syringe including a syringe needle having a needle, a fixing member for fixing the needle and an inner space formed in the fixing member, and a syringe body having a cylinder, a piston and a front end separably installed in the inner space of the fixing member of the syringe needle, the filter needle comprising:
   a filter structure installed in the inner space of the fixing member of the syringe needle so as to be prevented from being separated therefrom and including a one-way inlet path having an inlet and a one-way outlet path having an outlet, each of which has a check valve function, wherein the filter structure is configured to mount a filter and to provide a seal with the inner space of the fixing member such that medicament liquid passes the filter structure only through the inlet path and the outlet path; and
   a filter mounted to only the filter structure and installed in the outlet path at a rear end of the outlet to filter a foreign substance, which is input through the inlet together with a medicament liquid, from the medicament liquid such that the filtered medicament liquid is only injected into a patient through the filter and the outlet when injecting the medicament liquid into the patient.

2. The filter needle of claim 1, wherein the inlet path and the outlet path of the filter structure are closed.

3. The filter needle of claim 1, wherein the inlet path of the filter structure is an open inlet path and the outlet path of the filter structure is a closed outlet path.

4. The filter needle of claim 1, wherein the inlet path having the inlet of the filter structure is radially formed at an outside of the outlet path having the outlet such that a diameter of the outlet path is relatively larger than a diameter of the inlet path.

5. The filter needle of claim 1, wherein pillars are provided at an outside of the closed outlet path of the filter structure by a predetermined interval to form the open inlet path and the closed inlet path is formed as the filter structure is installed in the inner space of the fixing member of the syringe needle.

6. The filter needle of claim 5, wherein the closed outlet path of the filter structure includes the outlet formed by a cut line and the open inlet path includes an inclined film, which is foldable toward only one side, and is supported by at least one of the pillars to have the check valve function.

7. The filter needle of claim 1, wherein the open inlet path having an inclined film is formed at an outside of the closed outlet path of the filter structure, and a closed inlet path is formed as the filter structure is coupled to a guide groove formed on an inner wall in the inner space of the fixing member of the syringe needle.

8. The filter needle of claim 7, wherein the guide groove is formed across a step protrusion of the inner wall in the inner space, and an upper surface of the inclined film is closed to a lower end of the step protrusion formed with the guide groove, so that the check valve function is achieved.

9. The filter needle of claim 1, wherein the filter of the filter structure has a plane shape, a partition wall for fixing the filter protrudes more than the outlet path, and a radial opening is formed in the protruded partition wall to guide a liquid flow.

10. The filter needle of claim 1, wherein the filter installed into the outlet path of the filter structure is formed of a tubular body that forms the inner space.

11. The filter needle of claim 5, wherein the pillar of the filter structure protrudes more than a protruded curved surface where the outlet formed at a rear end of the outlet path is formed.

* * * * *